United States Patent [19]

Bornkamm et al.

[11] Patent Number: 5,639,596

[45] Date of Patent: Jun. 17, 1997

[54] DNA CONSTRUCT AND IN VITRO TEST FOR DETECTING TUMOR PROMOTERS BY MEANS OF SAID DNA CONSTRUCT

[75] Inventors: Georg Bornkamm; Axel Polack, both of München, Germany

[73] Assignee: GSF-Forschungszentrum fur Umweltund Gesundheit, Neuherberg, Germany

[21] Appl. No.: 196,259

[22] PCT Filed: Aug. 16, 1991

[86] PCT No.: PCT/DE91/00652

§ 371 Date: Jul. 25, 1994

§ 102(e) Date: Jul. 25, 1994

[87] PCT Pub. No.: WO93/04179

PCT Pub. Date: Mar. 4, 1993

[51] Int. Cl.[6] ............................ C12Q 1/68; C12Q 1/70
[52] U.S. Cl. ........................ 435/5; 435/6; 435/320.1
[58] Field of Search ........................ 435/5, 6, 320.1, 435/240.2, 235.1; 536/23.2, 23.4, 23.72

[56] References Cited

PUBLICATIONS

Cancer Research Clinical Oncology (Suppl. Part 1), vol. 116, Springer International, New York, US, p. 99; A. Polack et al: Description of an EBV system detecting tumor promoters of the diterpene esters type with high . . . .

Biological Abstracts, vol. 86, 1988: G.D. Kutuzova et al Synthesis of active luciferase of the glow worm *Luciola mingrelica* and its stability in the oocytes of the frog *Xenopus laevis*. p. 410.

Biochemical Society Transactions, vol. 18, No. 3, Jun. 1990, pp. 459–460; G. Sala–Newby et al: Production of translatable firefly luciferase mRNA in vitro from cloned cDNA.

Journal of Virology, vol. 56, No. 3, 1985, pp. 987–995; G. Laux et al: Structure and evolution of two related transcription units of Epstein–barr virus carrying small tandem repeats.

Molecular and Cellular Biology; vol. 5, No. 2, Feb. 1985 pp. 410–413; b. Sugden et al: A vector that replicates as a plasmid and can be efficiently selected in B–lymphoblasts transformed by Epstein–bar virus.

Biochimica et Biophysica Acta, vol. 949, 1988, pp. 206–212; A. Jalanko et al: An EBV–based mammalian cell expression vector for efficient expression of cloned coding sequences.

Chavrier et al., *J. Virol.*, vol. 63, 1989, pp. 607–614.

de Wet et al., *Mol. Cell. Biol.*, vol. 7, 1987, pp. 725–737.

Sambrook et al., *Molecular Cloning: A Laboratory Manual*, 2nd ed., 1989, pp. 16.33–16.37 and 16.59, CSH Laboratory Press, NY.

Takada et al., *International J. Cancer*, vol. 33, 1984, pp. 491–496.

zur Hausen et al., Proc. Natl. Acad. Sci. (USA), vol. 76, No. 2, pp. 782–785, Feb. 1979, "Tumor initiators and promoters in the induction of Epstein–Barr Virus."

*Primary Examiner*—James Ketter
*Attorney, Agent, or Firm*—Spencer & Frank

[57] ABSTRACT

The invention relates to a DNA construct and to a method of detecting tumor promoters by employing this DNA construct.

It is an object of the invention to make available an easily implemented quantitative detection method for tumor promoters.

This is accomplished by a DNA construct including at least one reporter gene and a control region for the activation of a particularly strongly induced gene of the Epstein-Barr virus (EBV), and by the action of the substance to be examined on EBV-containing cells that contain the DNA construct, whereupon the resulting quantity of reporter gene product is quantitatively determined.

13 Claims, 4 Drawing Sheets

5,639,596

DNA CONSTRUCT AND IN VITRO TEST FOR DETECTING TUMOR PROMOTERS BY MEANS OF SAID DNA CONSTRUCT

The invention relates to a DNA construct and to a method of detecting tumor promoters with the use of this DNA construct.

Tumor promoters are substances which, in combination with doses of solitary carcinogens that are in themselves not tumorigenic, induce the development of tumors or carcinomas. Solitary carcinogens are substances which produce tumors when applied individually (in animal tests) in dependence on the dosage. However, the sole influence of tumor promoters does not produce cancer in the sense of their definition, but it enhances to a considerable degree the development of tumors in organs which have been initiated by the exogenous influence of a solitary carcinogen. Simple and quickly performed tests systems are already available to identify solitary carcinogens. However, in the past, the substance class of tumor promoters could be identified only by way of animal experiments, for example, on the skin of a mouse or the intestines of a rat.

A starting procedure for a test to search out tumor promoters described by H. zur-Hausen, G. W. Bornkamm, R. Schmidt, and E. Hecker, entitled "Tumor Initiators and Promoters in the Induction of Epstein-Barr Virus", in Proceedings of the National Academic Science [sic] (U.S.A.), Volume 76, pages 782–785 (1979), provides for a determination of the property of substances that induces the Epstein-Barr virus (EBV) by means of an immunofluorescence display of EBV-coded antigens (so-called early antigens). However, this technique requires personnel that are trained in virology and serology procedures. Moreover, this process is time consuming and, due to the subjective evaluation of immunofluorescence stained cells, not accurately standardizable.

The final proof of the tumor promoting property of a substance can be brought only by the initiation of tumors in an in-vivo animal experiment, for example, on the skin of a mouse. However, such in-vivo experiments are not suitable as search tests for testing a plurality of substances.

It is now an object of the invention to make available a DNA construct and an easily performed quantitative method of the above-mentioned type.

This is accomplished by claims 1 and 8. The remaining claims define advantageous features of the invention.

The invention will now be described in greater detail with reference to two embodiments thereof and FIGS. 1 to 5.

FIG. 1 is a schematic representation of the configuration of the DNA construct, while

Figure 1:
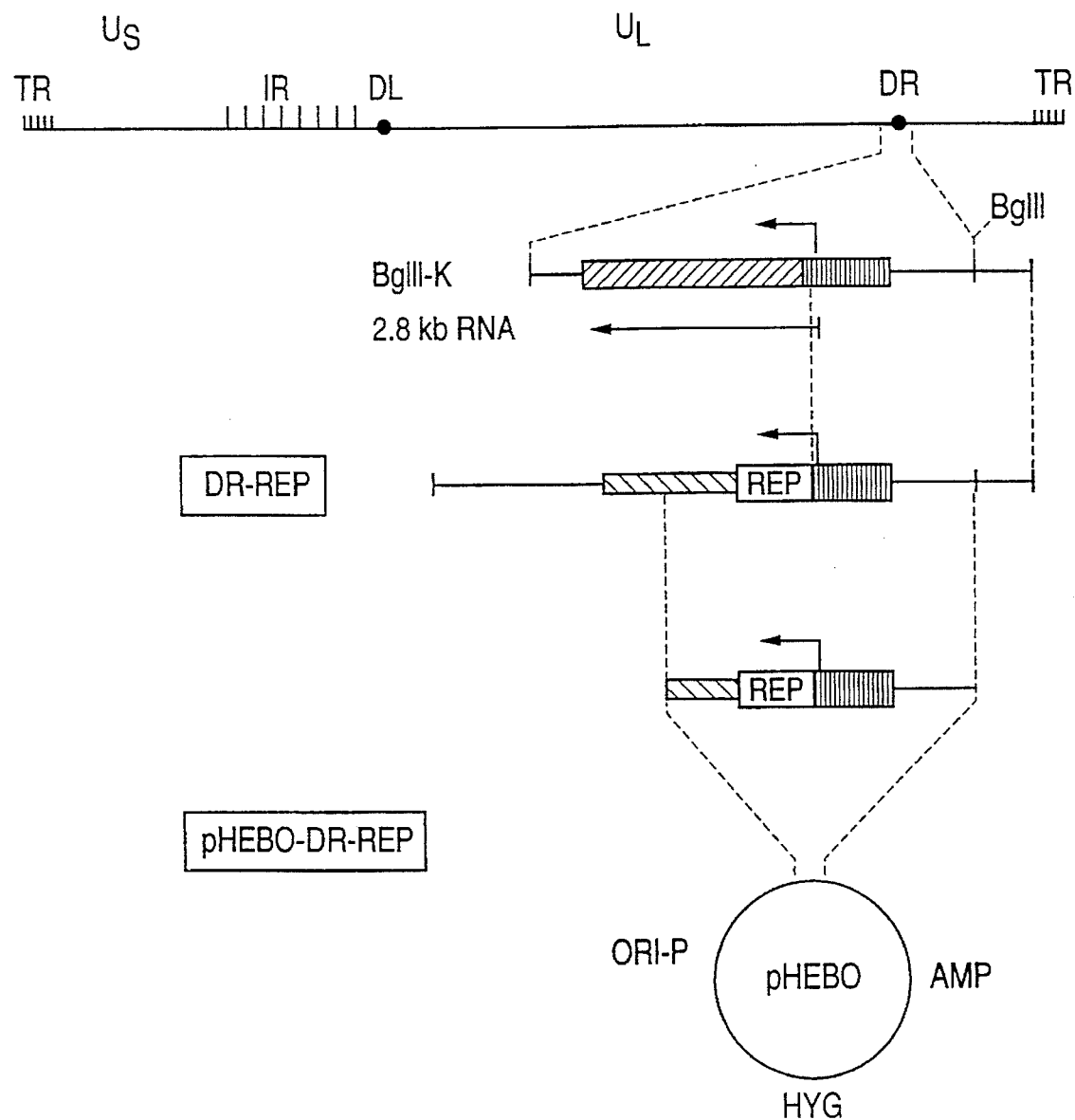
Figure 2:
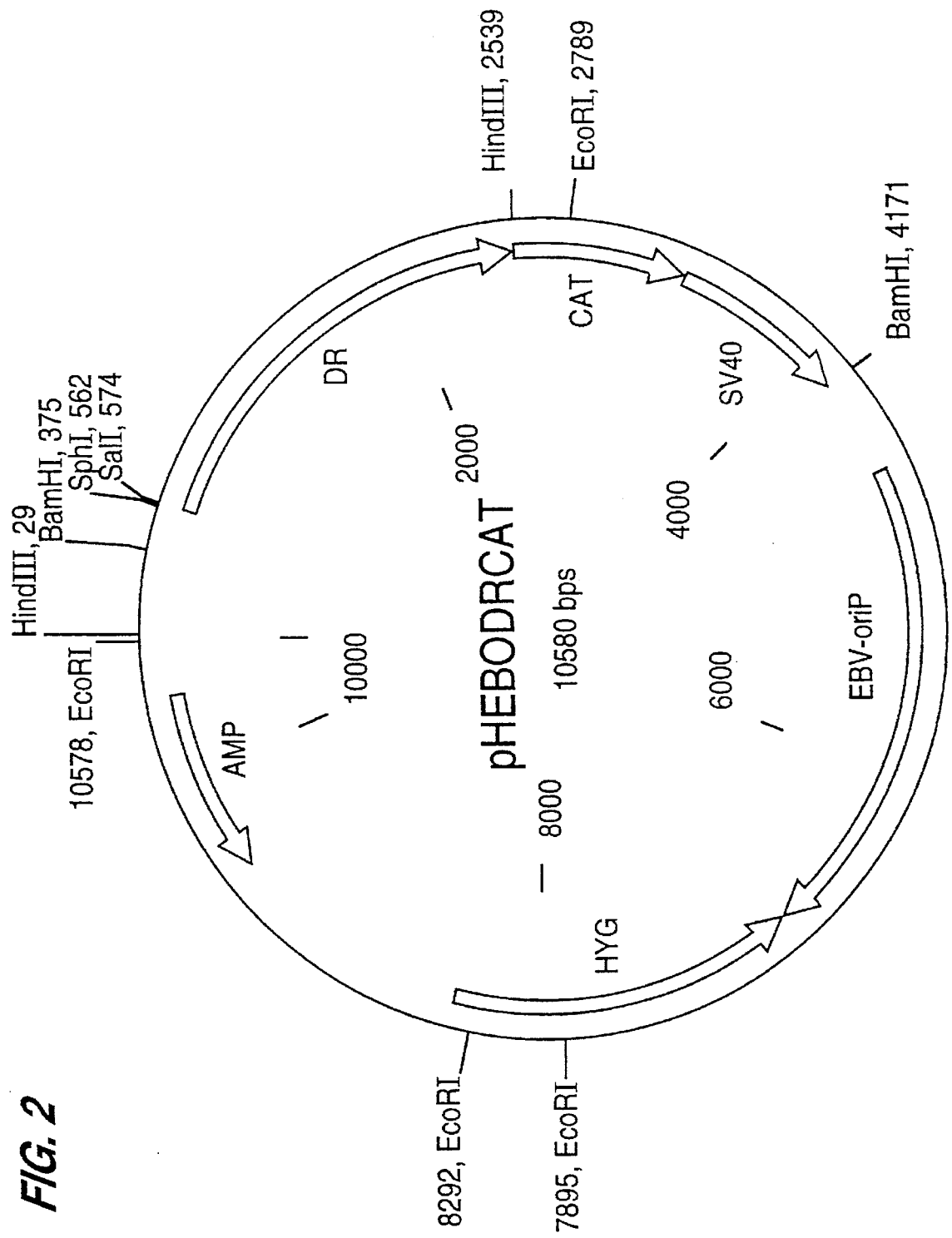
FIGS. 2 and 3 are schematic representations of two DNA constructs with points of intersection and their precise positions.
Figure 3:
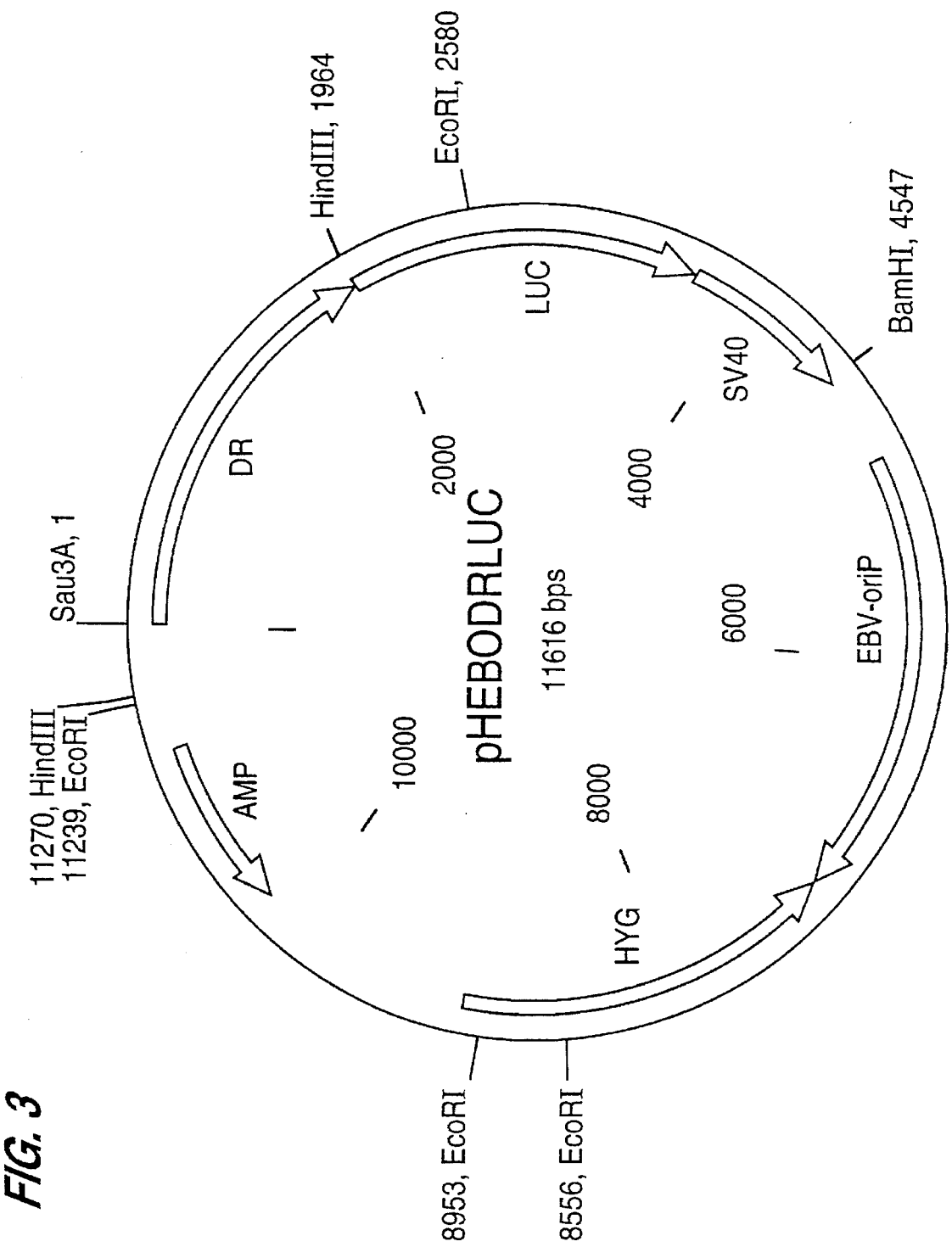

The base sequence (SEQ ID NOS: 1 and 2) and mapping of these two DNA constructs are given in Tables 1 and 2.

The invention is based on the observation that different classes of tumor promoters, such as diterpene esters, indole alkaloids or polyacetates, Teleocidin, transforming growth factor $\beta$ (TGF$\beta$), induce a lytic or abortive virus cycle in lymphatic cells containing the Epstein-Barr virus (EBV). The EBV genome contains a large number of genes that are not expressed in the latent state and are induced only upon the induction of a lytic or abortive cycle. The control region of the particularly strongly induced DR gene responsible for this activation (DL or others are possible) was cloned by molecular biology methods ahead of the coding region of a so-called reporter gene. The vector (pHEBO) employed for this purpose carries the episomal replication origin of EBV and two resistance genes one of which permits the selection of transfected eukaryotic cells with hygromycin and the other the selection in procaryotes.. This vector is described by B. Sugden, K. Marsh and J. A. Yates as "[A] vector that replicates as a plasmid and can be efficiently selected in B-lymphoblasts transformed by Epstein virus" in Molecular and Cellular Biology, Volume 5, pages 410–413 (1985). The construct obtained in this way (see also FIG. 1) was introduced in stable form into a cell line (Raji) containing EBV.

Raji cells were selected since, due to deletions, no infectious virus can be formed in the Raji-EBV genome, and because the so-called spontaneous induction rate in these cells is very low. Target cells for the stable transfection with the above-described plasmid can be all EBV positive cell lines which can be induced by chemical inductors (e.g., the cell line P3HR1 or Akata). The translation product of the reporter gene can be detected quantitatively in a relatively simple manner by way of an enzyme reaction in extracts of these cells. The quantity of detectable reporter gene product correlates quantitatively with the activation state of the EBV genome.

Due to the good correlation between tumor promoting and EBV inducing activity, this system can be employed as an easily and quickly performed search test for the identification of tumor promoters.

Tested were the reporter genes (REP) chloramphenicol acetyltransferase (CAT) and firefly luciferase (LUC).

Other usable reporter genes are: $\beta$-galactosidase, the $\beta$-globin gene, hepatitis B coded antigens, or the like.

The test system described here differs from the prior art systems primarily by its simplified implementation and a decisive improvement in the quantitative evaluation of the results. In the past, the subjective evaluation of immunofluorescence stained cells was included in each measuring result. In particular, the statement that a certain percentage of cells exhibits positive immunofluorescence for early EBV antigens includes a subjective determination of a threshold value. Moreover, the absolute protein quantity of early antigens developed in the individual cell cannot be determined in this way. In the past this made standardization considerably more difficult.

The quantity of resulting reporter gene product, however, can be determined accurately and reproducibly in a given number of cells. Another advantage of this system is the clonal origin of the stably transfected Raji-DR-REP line. It is known that during the long in-vitro cultivation of the Raji cell line, subpopulations are created which exhibit a different biological behavior. In addition, this test is distinguished by greater sensitivity and an improved dosage to effect ratio.

FIG. 1 is a diagram of the construction of the DNA clones (DNA constructs) DR-REP and pHEBO-DR-REP.

REP stands for reporter gene.

The top line in the drawing represents the genome of the EBV in linear form (terminal repetitions, TR; internal repetitions, IR; duplicated region left and right, DL and DR; long and short uniform region, $U_L$ and $U_S$). The next line is an enlarged representation of the BglII restriction fragment (BglII-K) (Polack et al, "A complete Set of Overlapping Cosmid Clones of M-ABA Virus Derived From Nasopharyngeal Carcinoma and Its Similarity to Other Epstein-Barr Virus Isolates" in Genes, Volume 27, pages 279–288, 1984), which carries the DR gene. The arrow in the next line corresponds to the messenger RNS of a size of 2.8 kb which was coded by this region.

The construction of pHEBO-DR-CAT with chloramphenicol acetyltransferase (CAT) as the reporter gene will now be described. The promoter region of the DR gene was cloned as a HindIII-NdeI fragment (after the conversion of the BglII point of intersection, which was disposed 3' away from the DR promoter, into a HindIII point of intersection) from pMBgllII-K ahead of the CAT reporter gene at the points of intersection HindIII/NdeI of the pSV2CAT vector (the SV40 promoter in the pSV2CAT was thus deleted).

The DR-promoter-CAT component of the DR-CAT clone was inserted as an XbaI-BamHI fragment at the points of intersection BamH I and XbaI of the puc18(R/X) vector (laboratory identification: G3-28). The puc18(R/X) vector developed from the conversion of the EcoR I point of intersection into an XhoI point of intersection in vector puc18. From Ge-28, DR-CAT was mobilized as an SphI-XhoI fragment and cloned into the SphI/SalI point of intersection of vector pHEBO (pHEBO-DR-CAT).

The promoter of the DR gene is identified as a black box. The point of initiation of polymerase II is represented by a short arrow oriented toward the left. The SV40 component, 3' removed from the open reading frame of the CAT gene, is shown in hatching. The term ori-P represents the "origin of plasmid replication" of EBV, HYG stands for the hygromycin resistance gene and AMP for the resistance gene against ampicillin.

Figure 4:
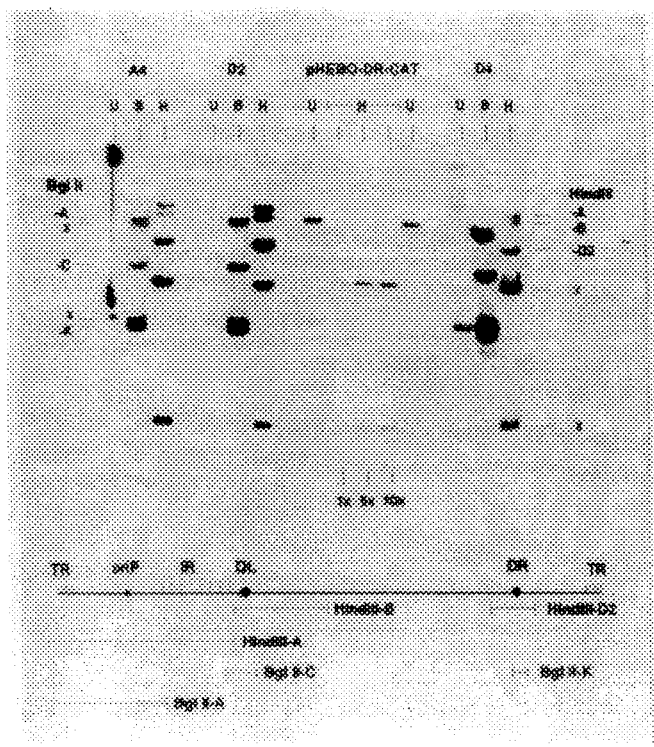
FIG. 4 shows a Southern-blot analysis of various pHEBO-DR-CAT transfectants (A4, D2, D4)

FIG. 4 shows a Southern-blot analysis of various pHEBO-DR-CAT transfectants (A4, D2, D4).

In each case, approximately 10 µg of cellular DNA of sublines A4, D2 and D4 were applied either unsplit (U) or split with BglII (B) or HindIII (H), onto an 0.6% agarose gel. The unsplit (U) and the HindIII (H) split plasmid pHEBO-CR-CAT, respectively, served as a control, of which a one-fold (1x), five-fold (5x) and ten-fold (10x) amount of a genome equivalent was applied. After the gel run, the DNA, which was separated according to size, was transferred to nitrocellulose filters and hybridized with $^{32}$P-marked DNA of pHEBO-DR-CAT. The cloned pHEBO-DR-CAT contains sequences which hybridize with the oriP as well as with EBV regions DL and DR.

In the cellular DNAs (A4, D2, D4) cut with HindIII, there appear five bands in the autoradiogram: the HindIII fragments A, B and D2 of the endogenous Raji-EBV genome, and two fragments of a size of 8 and 2.5 kb corresponding to the transfected DNA (marked x; see right margin). The BglII fragments A, C and K of the endogenous Raji EBV genome are represented through Bgl II digestion. Since Bgl II does not intersect in the cloned pHEBO-DR-CAT, the identical band pattern as in the unsplit applied plasmid (pHEBO-DR-CAT: U) results for the transfected DNA (marked with an x at the left margin of the autoradiogram).

The result of this Southern-blot analysis leads to the conclusion that the transfected plasmid is contained in the episomal state and in about 50 to 100 copies in all three sublines.

A simplified restriction enzyme map of the EBV genome is represented below the autoradiogram.

Figure 5:
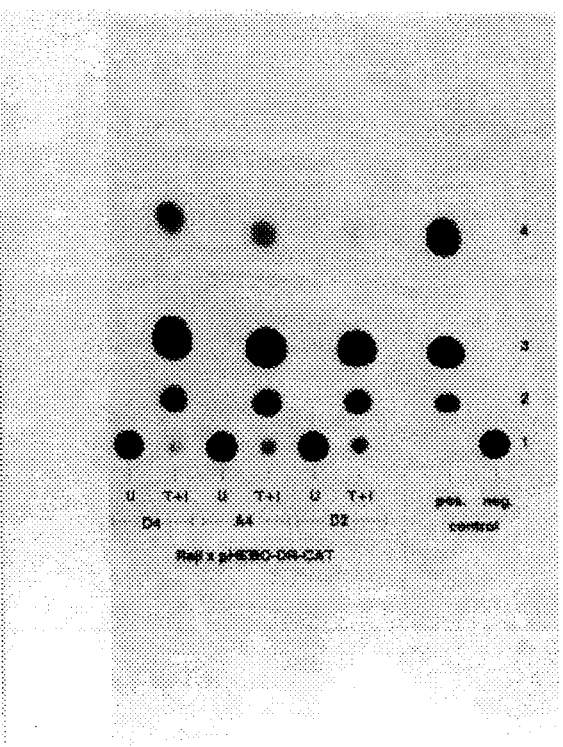
FIG. 5 depicts a CAT assay of the pHEBO-DR-CAT transfected Raji sublines D4, A4 and D2.

FIG. 5 depicts a CAT assay of the pHEBO-DR-CAT transfected Raji sublines D3, A4 and D2.

Approximately 20 to $30 \times 10^6$ cells were treated for 48 hours with the tumor promoter TPA (20 ng/ml sigma) and 5-iodo-2'desoxyuridin (50 µg/ml sigma) as intensifier. The CAT enzyme developed only in the induced cells (T+I) as indicated by the occurrence of acetylized forms (marked with 2, 3, 4 in the right margin) of the $^{14}$C-marked chloramphenicol in the enzyme assay. No CAT activity can be detected in untreated cells (U).

The detection of tumor promoting properties of compounds (detection of tumor promoters) for both variations is effected according to the following schemes.

(a) Raji Cells Transfected with pHEBO-DR-CAT (1) growing at least 1 to $5 \times 10^6$ transfected cells per experiment;
cell culture conditions:
cell culture medium: RPMI 1640 (Gibco) with: approximately 10% fetal calf serum, 300 µg/ml hygromycin (Calbiochem), 100 u/ml penicillin, 280 µg/ml L-glutamine, approximately 37° C., 5 to 6% $CO_2$.
(2) incubation of these cells with a corresponding quantity of the substance to be tested for 48 hours (=standard starting mixture; <20 hours up to several days are also possible) at 37° C. and in 6% $CO_2$;
(3) recovery of the cells by centrifuging;
(4) resuspension of the cells in 100 µl 0.25M tris-HCl (pH 7.8);
(5) break-up of the cells to obtain the developed enzyme by means of ultrasound treatment or three cycles of freezing/thawing (3 minutes in a $CO_2$/ethanol bath/3 minutes thawing at 30° C.);
(6) clarification the cell lysate by centrifuging;
(7) determination of the protein concentration;
(8) incubation of, for example,
20 µl lysate (quantity depends on the protein quantity);
100 µl 0.25M tris-HCl (pH 7.8);
1 µCi $^{14}$C-chloramphenicol;
20 µl 4 mM acetyl coenzyme A;
(9) incubation at 37° C. for one hour (longer incubation may increase sensitivity somewhat);
(10) interruption of the enzyme reaction by the addition of 2 ml cold ethyl acetate;
(11) intensive mixing of the reaction mixture for extraction of the chloramphenicol and the developed derivatives;
(12) centrifugation in order to separate the phases;
(13) removal of the organic phase;
(14) inspissation of the organic phase from (13) by applying a vacuum with simultaneous rotation;
(15) resuspension of the remaining solid phases from (14) in 30 µl ethyl acetate;
(16) thin film chromatography with chloroform ethanol (95:5) as the running agent for the separation of the different acetylized forms of chloramphenicol on silica gel plates (Polygram Sil G, Macherey-Nagel);
(17) autoradiography of the thin-film chromatography plates or evaluation with the aid of a radioactivity scanner.

(b) Raji Cells Transfected with pHEBO-DR-LUC (1) growing at least 0.1 to $1.0 \times 10^4$ transfected cells per experiment;
cell culture conditions:
cell culture medium: RPMI 1640 (Gibco) with: 10% fetal calf serum, 300 µg/ml hygromycin (Calbiochem), 100 u/ml penicillin, 280 µg/ml L-glutamine, 37° C., 5 to 6% $CO_2$;

(2) incubation of these cells with a corresponding quantity of substance to be tested for 48 hours (=standard starting mixture; <20 hours up to several days is also possible) at 37° C. and in 6% $CO_2$;
(3) recovery of the cells by centrifuging;
(4) resuspension of the cells in lyse buffer (100 mM potassium phosphate, ph 7.8, 1 mM DTT);
(5) break-up of the cells to obtain the developed enzyme by means of ultrasound treatment of three cycles of freezing/thawing (3 minutes in a $CO_2$/ethanol bath/3 minutes thawing at 30° C.);
(6) clarification of the cell lysate by centrifuging;
(7) determination of the protein concentration;
(8) incubation of, for example,
    20 µl lysate (quantity depends on the protein quantity);
    100 µl test buffer (25 mM glycyl glycine, pH 7.8; 5 mMATP, 15 mMMgSo$_4$);
injection of
    100 µl luciferin solution (1 mM luciferin in 0.5M tris-Hcl (pH 7.8);
(9) immediate measurement of the emitted light in a luminometer (e.g., Lumat by Berthold).

The quantity of the detected enzymes is a measure for the EBV-inducing property of the examined substances and thus permits a conclusion as to the possible tumor promoting property of this substance.

The particular advantages of method (b) over method (a) are the significantly lower quantity of cells, a sensitivity that is higher by a multiple, a significantly simplified quantifiability (the quantity of resulting enzyme can be quantitatively determined in a luciferase test through several logging stages without additional dilution series), a noticeably lower amount of work involved and the avoidance of radioactive waste.

TABLE 1 pHEBO-DR-CAT

| Features: | |
|---|---|
| Identification in record book: | DRCATPHEBO |
| Cloning: | DR-CAT as XhoI-SphI 3.6 kb fragment cloned into SalI-SphI of pHEBO |
| Total bases: | 10,580 |
| Restriction Enzyme Intersections: | Position: |
| HindIII | 29 |
| BamHI | 375 |
| SphI | 562 |
| SalI | 574 |
| HindIII | 2,539 |
| EcoRI | 2,789 |
| BamHI | 4,171 |
| EcoRI | 7,895 |
| EcoRI | 8,292 |
| EcoRI | 10,578 |
| Regions: | Position: |
| DR | 575–2,539 |
| CAT | 2,539–3,325 |
| SV40 | 3,325–4,171 |
| EBV-oriP | 4,603–6,783 |
| hygromycin resistance gene | 8,383–6,783 |
| ampicillin resistance gene | 10,333–9,483 |

Sequence (SEQ ID NO: 1):
TTCTCATGTTTGACAGCTTATCATCGATAAGCTTTAATGCGGTAGTTTATCACAGTTAAATT
GCTAACGCAGTCAGGCACCGTGTATGAAATCTAACAATGCGCTCATCGTCATCCTCGGCACC
GTCACCCTGGATGCTGTAGGCATAGGCTTGGTTATGCCGGTACTGCCGGGCCTCTTGCGGGA
TATCGTCCATTCCGACAGCATCGCCAGTCACTATGGCGTGCTGCTAGCGCTATATGCGTTGA
TGCAATTTCTATGCGCACCCGTTCTCGGAGCACTGTCCGACCGCTTTGGCCGCCGCCCAGTC
CTGCTCGCTTCGCTACTTGGAGCCACTATCGACTACGCGATCATGGCGACCACACCCGTCCT
GTGGATCCTCTACGCCGGACGCATCGTGGCCGGCATCACCGGCGCCACAGGTGCGGTTGCTG
GCGCCTATATCGCCGACATCACCGATGGGGAAGATCGGGCTCGCCACTTCGGGCTCATGAGC
GCTTGTTTCGGCGTGGGTATGGTGGCAGGCCCCGTGGCCGGGGGACTGTTGGGCGCCATCTC
CTTGCATGCCTGCAGGTCGACTCTAGAACTGGATACTCGTGGGGGGTAAAGAAGGTGAATAA
AAATTACAAACATTCTCTGCCCAGCCTTCAGACTATCAAACCTAGATAATCATTCTATAAAT
AACCCAGGGCTTGCATCACAATTTAAAGGGAAGTTAAGATGGGGGATTACCTTCTAAGAGGA
AATGACAAGCCACAGACATCCCCACATATAGCCGGGTGTCCACTGTCTAATGTCAGTAATTT
AATTCCATAGTGAAAATAGCACCCCCAACTCAATTTGGAATCCAGAAACTATATTGCACACC
AACACCCCCTCCTCTGCACATGAGCAAGACAAGACATCTATGTTTATCTCTAAATGTGCCAT
GGAACCCGGTTGCCCATGCAGTGGTGTCAGACAGGAAAATGGTTAATTAACCACATCTTAAA
TTGCCACCTTAGGCAAATTGAAAATAGGCAGGCTGAAGAATTGCACAATACCCTAAACAGGT
AAGAGGAATTAGTGACATTTTATGAATTTTTTTACAAACTTTCACACTCAAGAATAGAAACC
CAATACCAACAGGTGTGCAGGTGTGCATGACAAATCTTGGGGGTCTCAGAACCCAGGACCAG
ACTTTGAAGTCTCAGGTATAGGTCCTGGCTGAGATTCTATTAATAAAACAAGAGAGAAAGAA
GGCGGGCGCCCATTAGAATCTGCTCGGCTGCCAGTAAGTTGCCAGCAAACAGGAACACAAAC
AAACCAAGGGTGTTGGCCCCTACAGGCTCCCAAGGCGGGGGTTGGGCACAGGGCCAAGCTCT
GCCACCACAGGAGGCAAGTAGACATGCAGGAACACATGGCCCTGGCTAGGAAAGGGAGGAAA
TAGAGGCCACAGCCAAAGTTAGGCTGCCGCCCCACCTGTGTACCCAGGGTGAGAGACCTTGG
GAGGTCGTCAGCTTAACCAGCGCCGCCCTCACCCCATTGCCAACTTCCGGCTCACACAAAAC
CACTCCCAAAAATTGAAGACTGGCCAAAATCCAGCTTCCGTCCCCGGGACGTGGTGCTTCCT
AAAGGCGGGGCTCATGGATTAGCAGGGGCTTAGTGTGTCATGGTGAGGCAGGCAAGGCGAGC
AACGGGGGCTTAGTGGCTCAAAGTGATGCATCCCAAAGGCAGCCACCACGCTGGAGGGACAT TABLE 1-continued pHEBO-DR-CAT

```
TGTCCACGGGACAAGGCACAGGCCAGGTCATGACCCAGGAAGTGGCGAGCATCGGTCAGCTG
ACCAAATGTGCAAAGGTGACAAGTCAGTAAGGCACGCGGGGGGCCACGTCACCCCGGGGTGC
TGGGGTGGGGGATGGGCTCAGGCAACCGTAAGGGAGGGGGGGGTAGGGGGGGGAGGGATTAC
ACTATAGGGTTCCCTTCCTCTAGGTTCTATATACCTATAGGTATATACCCAGCTGCAATACC
CTATTCCACCACTAGGTTAATAACCTATAGGTTATTCTACCATTAAAACGGAAGGAGGAAGG
GTGGCGCACCTTAAGGTAGGGTAGGGGGGTACCCCAGTAGGAACCTAGCTGAATCCTACCTA
GCTCCACCCACCTGGTATATAGGGGCGGAGCTTAGGATACCTCCAGGATAATGGAACCCTAT
GGAGACCTACCTCTAGGCTCCACCCACTAGGTATATCGGGGCGGAGCCCACTCCTCCCCCTC
CTGGTTCAACCCTATGGAGGGGACCCTCCTGAGGCTCCGCCTACCCCAAATCTCGCGGGCCT
CTAGCCCCTCCTCCTCTCGTTATCCCAATAGAATGACCTCCAGGTACCACCCACCTGGTTAC
ACACCTTAATGTAACCCAACGGGCTAAAATCACACACCTGAATTAACCAATGAGAAGCCCCC
CACACCTGAGCAAACCTTAAGGTATTGCACAGAAACCCCAAAAAGAGGATAAAAGAAGGCGA
GCTGGCCCGGCTCGCCAGCGTCGTCCAGACGCTCGGGGGGTGCACACCTCCCAGCCGCAAGC
TTGGCGAGATTTTCAGGAGCTAAGGAAGCTAAAATGGAGAAAAAAATCACTGGATATACCAC
CGTTGATATATCCCAATGGCATCGTAAAGAACATTTTGAGGCATTTCAGTCAGTTGCTCAAT
GTACCTATAACCAGACCGTTCAGCTGGATATTACGGCCTTTTTAAAGACCGTAAAGAAAAAT
AAGCACAAGTTTTATCCGGCCTTTATTCACATTCTTGCCCGCCTGATGAATGCTCATCCGGA
ATTCCGTATGGCAATGAAAGACGGTGAGCTGGTGATATGGGATAGTGTTCACCCTTGTTACA
CCGTTTTCCATGAGCAAACTGAAACGTTTTCATCGCTCTGGAGTGAATACCACGACGATTTC
CGGCAGTTTCTACACATATATTCGCAAGATGTGGCGTGTTACGGTGAAAACCTGGCCTATTT
CCCTAAAGGGTTTATTGAGAATATGTTTTTCGTCTCAGCCAATCCCTGGGTGAGTTTCACCA
GTTTTGATTTAAACGTGGCCAATATGGACAACTTCTTTCGCCCCCGTTTTCACCATGGGCAAA
TATTATACGCAAGGCGACAAGGTGCTGATGCCGCTGGCGATTCAGGTTCATCATGCCGTCTG
TGATGGCTTCCATGTCGGCAGAATGCTTAATGAATTACAACAGTACTGCGATGAGTGGCAGG
GCGGGGCGTAATTTTTTAAGGCAGTTATTGGTGCCCTTAAACGCCTGGTGCTACGCCTGAA
TAAGTGATAATAAGCGGATGAATGGCAGAAATTCGCCGGATCTTTGTGAAGGAACCTTACTT
CTGTGGTGTGACATAATTGGACAAACTACCTACAGAGATTTAAAGCTCTAAGGTAAATATAA
AATTTTTAAGTGTATAATGTGTTAAACTACTGATTCTAATTGTTTGTGTATTTTAGATTCCA
ACCTATGGAACTGATGAATGGGAGCAGTGGTGGAATGCCTTTAATGAGGAAAACCTGTTTTG
CTCAGAAGAAATGCCATCTAGTGATGATGAGGCTACTGCTGACTCTCAACATTCTACTCCTC
CAAAAAAGAAGAGAAAGGTAGAAGACCCCAAGGACTTTCCTTCAGAATTGCTAAGTTTTTTG
AGTCATGCTGTGTTTAGTAATAGAACTCTTGCTTGCTTTGCTATTTACACCACAAAGGAAAA
AGCTGCACTGCTATACAAGAAAATTATGGAAAAATATTCTGTAACCTTTATAAGTAGGCATA
ACAGTTATAATCATAACATACTGTTTTTTCTTACTCCACACAGGCATAGAGTGTCTGCTATT
AATAACTATGCTCAAAAATTGTGTACCTTTAGCTTTTTAATTTGTAAAGGGGTTAATAAGGA
ATATTTGATGTATAGTGCCTTGACTAGAGATCATAATCAGCCATACCACATTTGTAGAGGTT
TTACTTGCTTTAAAAAACCTCCCACACCTCCCCCTGAACCTGAAACATAAAATGAATGCAAT
TGTTGTTGTTAACTTGTTTATTGCAGCTTATAATGGTTACAAATAAAGCAATAGCATCACAA
ATTTCACAAATAAAGCATTTTTTTCACTGCATTCTAGTTGTGGTTTGTCCAAACTCATCAAT
GTATCTTATCATGTCTGGATCCCCGGGTACCGAGCTCGCCTCGACCGATGCCCTTGAGAGCC
TTCAACCCAGTCAGCTCCTTCCGGTGGGCGCGGGGCATGACTATCGTCGCCGCACTTATGAC
TGTCTTCTTTATCATGCAACTCGTAGGACAGGTGCCCTGGCCGGGGTCCCGCGGAAACTCGG
CCGTGGTGACAGGAAAAGGACAAGCAGCGAAAATTCACGCCCCCTTGGGAGGTGGCGGCATA
TGCAAAGGATAGCACTCCCACTCTACTACTGGGTATCATATGCTGACTGTATATGCATGAGG
ATAGCATATGCTACCCGGATACAGATTAGGATAGCATATACTACCCAGATATAGATTAGGAT
AGCATATGCTACCCAGATATAGATTAGGATAGCCTATGCTACCCAGATATAAATTAGGATAG
CATATACTACCCAGATATAGATTAGGATAGCATATGCTACCCAGATATAGATTAGGATAGCC
TATGCTACCCAGATATAGATTAGGATAGCATATGCTACCCAGATATAGATTAGGATAGCATA
TGCTATCCAGATATTTGGGTAGTATATGCTACCCAGATATAAATTAGGATAGCATATACTAC
CCTAATCTCTATTAGGATAGCATATGCTACCCGGATACAGATTAGGATAGCATATACTACCC
AGATATAGATTAGGATAGCATATGCTACCCAGATATAGATTAGGATAGCCTATGCTACCCAG
ATATAAATTAGGATAGCATATACTACCCAGATATAGATTAGGATAGCATATGCTACCCAGAT
ATAGATTAGGATAGCCTATGCTACCCAGATATAGATTAGGATAGCATATGCTATCCAGATAT
TTGGGTAGTATATGCTACCCATGGCAACATTAGCCCACCGTGCTCTCAGCGACCTCGTGAAT
ATGAGGACCAACAACCCTGTGCTTGGCGCTCAGGCGCAAGTGTGTGTAATTTGTCCTCCAGA
TCGCAGCAATCGCGCCCCTATCTTGGCCCGCCCACCTACTTATGCAGGTATTCCCCGGGGTG
CCATTAGTGGTTTTGTGGGCAAGTGGTTTGACCGCAGTGGTTAGCGGGGTTACAATCAGCCA
AGTTATTACACCCTTATTTTACAGTCCAAAACCGCAGGGCGGCGTGTGGGGGCTGACGCGTG
CCCCCACTCCACAATTTCAAAAAAAAGAGTGGCCACTTGTCTTTGTTTATGGGCCCCATTGG
CGTGGAGCCCCGTTTAATTTTCGGGGGTGTTAGAGACAACCAGTGGAGTCCGCTGCTGTCGG
CGTCCACTCTCTTTCCCCTTGTTACAAATAGAGTGTAACAACATGGTTCACCTGTCTTGGTC
CCTGCCTGGGACACATCTTAATAACCCCAGTATCATATTGCACTAGGATTATGTGTTGCCCA
TAGCCATAAATTCGTGTGAGATGGACATCCAGTCTTTACGGCTTGTCCCCACCCCATGGATT
TCTATTGTTAAAGATATTCAGAATGTTTCATTCCTACACTAGTATTTATTGCCCAAGGGGTT
TGTGAGGGTTATATTGGTGTCATAGCACAATGCCACCACTGAACCCCCCGTCCAAATTTTAT
TCTGGGGGCGTCACCTGAAACCTTGTTTTCGAGCACCTCACATACACCTTACTGTTCACAAC
TCAGCAGTTATTCTATTAGCTAAACGAAGGAGAATGAAGAAGCAGGCGAAGATTCAGGAGAG
TTCACTGCCCGCTCCTTGATCTTCAGCCACTGCCCTTGTGACTAAAATGGTTCACTACCCTC
GTGGAATCCTGACCCCATGTAAATAAAACCGTGACAGCTCATGGGGTGGGAGATATCGCTGT
TCCTTAGGACCCTTTTACTAACCCTAATTCGATAGCATATGCTTCCCGTTGGGTAACATATG
CTATTGAATTAGGGTTAGTCTGGATAGTATATACTACTACCCGGGAAGCATATGCTACCCGT
TTAGGGTTAACAAGGGGGCCTTATAAACACTATTGCTAATGCCCTCTTGAGGGTCCGCTTAT
CGGTAGCTACACAGGCCCCTCTGATTGACGTTGGTGTAGCCTCCCGTAGTCTTCCTGGGCCC
CTGGGAGGTACATGTCCCCCAGCATTGGTGTAAGAGCTTCAGCCAAGAGTTACACATAAAGG
CAATGTTGTGTTGCAGTCCACAGACTGCAAAGTCTGCTCCAGGATGAAAGCCACTCAGTGTT
GGCAAATGTGCACATCCATTTATAAGGATGTCAACTACAGTCAGAGAACCCCTTTGTGTTTG
GTCCCCCCCCGTGTCACATGTGGAACAGGGCCCAGTTGGCAAGTTGTACCAACCAACTGAAG
```

TABLE 1-continued pHEBO-DR-CAT

```
GGATTACATGCACTGCCCCGTGACCAATACAAAACAAAAGCGCTCCTCGTACCAGCGAAGAA
GGGGCAGAGATGCCGTAGTCAGGTTTAGTTCGTCCGGCGGCGCCAGAAATCCGCGCGGTGGT
TTTTGGGGGTCGGGGGTGTTTGGCAGCCACAGACGCCCGGTGTTCGTGTCGCGCCAGTACAT
GCGGTCCATGCCCAGGCCATCCAAAAACCATGGGTCTGTCTGCTCAGTCCAGTCGTGGACCT
GACCCCACGCAACGCCCAAAAGAATAACCCCCACGAACCATAAACCATTCCCCATGGGGGAC
CCCGTCCCTAACCCACGGGGCCCGTGGCTATGGCGGGCTTGCCGCCCCGACGTTGGCTGCGA
GCCCTGGGCCTTCACCCGAACTTGGGGGTTGGGGTGGGGAAAAGGAAGAAACGCGGGCGTAT
TGGCCCCAATGGGGTCTCGGTGGGGTATCGACAGAGTGCCAGCCCTGGGACCGAACCCCGCG
TTTATGAACAAACGACCCAACACCCGTGCGTTTTATTCTGTCTTTTTATTGCCGTCATAGCG
CGGGTTCCTTCCGGTATTGTCTCCTTCCGTGTTTCAGTTAGCCTCCCCCATCTCCCGATCCC
CTCGGACGAGTGCTGGGGCGTCGGTTTCCACTATCGGCGAGTACTTCTACACAGCCATCGGT
CCAGACGGCCGCGCTTCTGCGGGCGATTTGTGTACGCCCGACAGTCCCGGCTCCGGATCGGA
CGATTGCGTCGCATCGACCCTGCGCCCAAGCTGCATCATCGAAATTGCCGTCAACCAAGCTC
TGATAGAGTTGGTCAAGACCAATGCGGAGCATATACGCCCGGAGCCGCGGCGATCCTGCAAG
CTCCGGATGCCTCCGCTCGAAGTAGCGCGTCTGCTGCTCCATACAAGCCAACCACGGCCTCC
AGAAGAAGATGTTGGCGACCTCGTATTGGGAATCCCCGAACATCGCCTCGCTCCAGTCAATG
ACCGCTGTTATGCGGCCATTGTCCGTCAGGACATTGTTGGAGCCGAAATCCGCGTGCACGAG
GTGCCGGACTTCGGGGCAGTCCTCGGCCCAAAGCATCAGCTCATCGAGAGCCTGCGCGACGG
ACGCACTGACGGTGTCGTCCATCACAGTTTGCCAGTGATACACATGGGGATCAGCAATCGCG
CATATGAAATCACGCCATGTAGTGTATTGACCGATTCCTTGCGGTCCGAATGGGCCGAACCC
GCTCGTCTGGCTAAGATCGGCCGCAGCGATCGCATCCATGGCCTCCGCGACCGGCTGCAGAA
CAGCGGGCAGTTCGGTTTCAGGCAGGTCTTGCAACGTGACACCCTGTGCACGGCGGGAGATG
CAATAGGTCAGGCTCTCGCTGAATTCCCCAATGTCAAGCACTTCCGGAATCGGGAGCGCGGC
CGATGCAAAGTGCCGATAAACATAACGATCTTTGTAGAAACCATCGGCGCAGCTATTTACCC
GCAGGACATATCCACGCCCTCCTACATCGAAGCTGAAAGCACGAGATTCTTCGCCCTCCGAG
AGCTGCATCAGGTCGGAGACGCTGTCGAACTTTTCGATCAGAAACTTCTCGACAGACGTCGC
GGTGAGTTCAGGCTTTTTCATATCTCATTGCCCCCGGGGGATCTGCGGCACGCTGTTGACGC
TGTTAAGCGGGTCGCTGCAGGGTCGCTCGGTGTTCGAGGCCACACGCGTCACCTTAATATGC
GAAGTGGACCTGGGACCGCGCCGCCCGACTGCATCTGCGTGTTCGAATTCGCCAATGACAA
GACGCTGGGCGGGGTTTGTGTCATCATAGAACTAAAGACATGCAAATATATTTCTTCCGGGG
ACACCGCCAGCAAACGCGAGCAACGGGCCACGGGGATGAAGCAGGGCGGCACCTCGCTAACG
GATTCACCACTCCAAGAATTGGAGCCAATCAATTCTTGCGGAGAACTGTGAATGCGCAAACC
AACCCTTGGCAGAACATATCCATCGCGTCCGCCATCTCCAGCAGCCGCACGCGGCGCATCTC
GGGCAGGCCGACGCGCTGGGCTACGTCTTGCTGGCGTTCGCGACGCGAGGCTGGATGGCCTT
CCCCATTATGATTCTTCTCGCTTCCGGCGGCATCGGGATGCCCGCGTTGCAGGCCATGCTGT
CCAGGCAGGTAGATGACGACCATCAGGGCAGCAAAAGGCCAGGAACCGTAAAAAGGCCGCGT
TGCTGGCGTTTTTCCATAGGCTCCGCCCCCCTGACGAGCATCACAAAAATCGACGCTCAAGT
CAGAGGTGGCGAAACCCGACAGGACTATAAAGATACCAGGCGTTTCCCCCTGGAAGCTCCCT
CGTGCGCTCTCCTGTTCCGACCCTGCCGCTTACCGGATACCTGTCCGCCTTTCTCCCTTCGG
GAAGCGTGGCGCTTTCTCAATGCTCACGCTGTAGGTATCTCAGTTCGGTGTAGGTCGTTCGC
TCCAAGCTGGGCTGTGTGCACGAACCCCCCGTTCAGCCCGACCGCTGCGCCTTATCCGGTAA
CTATCGTCTTGAGTCCAACCCGGTAAGACACGACTTATCGCCACTGGCAGCAGCCACTGGTA
ACAGGATTAGCAGAGCGAGGTATGTAGGCGGTGCTACAGAGTTCTTGAAGTGGTGGCCTAAC
TACGGCTACACTAGAAGGACAGTATTTGGTATCTGCGCTCTGCTGAAGCCAGTTACCTTCGG
AAAAAGAGTTGGTAGCTCTTGATCCGGCAAACAAACCACCGCTGGTAGCGGTGGTTTTTTTG
TTTGCAAGCAGCAGATTACGCGCAGAAAAAAAGGATCTCAAGAAGATCCTTTGATCTTTTCT
ACGGGGTCTGACGCTCAGTGGAACGAAAACTCACGTTAAGGGATTTTGGTCATGAGATTATC
AAAAAGGATCTTCACCTAGATCCTTTTAAATTAAAAATGAAGTTTTAAATCAATCTAAAGTA
TATATGAGTAAACTTGGTCTGACAGTTACCAATGCTTAATCAGTGAGGCACCTATCTCAGCG
ATCTGTCTATTTCGTTCATCCATAGTTGCCTGACTCCCCGTCGTGTAGATAACTACGATACG
GGAGGGCTTACCATCTGGCCCCAGTGCTGCAATGATACCGCGAGACCCACGCTCACCGGCTC
CAGATTTATCAGCAATAAACCAGCCAGCCGGAAGGGCCGAGCGCAGAAGTGGTCCTGCAACT
TTATCCGCCTCCATCCAGTCTATTAATTGTTGCCGGGAAGCTAGAGTAAGTAGTTCGCCAGT
TAATAGTTTGCGCAACGTTGTTGCCATTGCTGCAGGCATCGTGGTGTCACGCTCGTCGTTTG
GTATGGCTTCATTCAGCTCCGGTTCCCAACGATCAAGGCGAGTTACATGATCCCCCATGTTG
TGCAAAAAAGCGGTTAGCTCCTTCGGTCCTCCGATCGTTGTCAGAAGTAAGTTGGCCGCAGT
GTTATCACTCATGGTTATGGCAGCACTGCATAATTCTCTTACTGTCATGCCATCCGTAAGAT
GCTTTTCTGTGACTGGTGAGTACTCAACCAAGTCATTCTGAGAATAGTGTATGCGGCGACCG
AGTTGCTCTTGCCCGGCGTCAACACGGGATAATACCGCGCCACATAGCAGAACTTTAAAAGT
GCTCATCATTGGAAAACGTTCTTCGGGGCGAAAACTCTCAAGGATCTTACCGCTGTTGAGAT
CCAGTTCGATGTAACCCACTCGTGCACCCAACTGATCTTCAGCATCTTTTACTTTCACCAGC
GTTTCTGGGTGAGCAAAAACAGGAAGGCAAAATGCCGCAAAAAAGGGAATAAGGGCGACACG
GAAATGTTGAATACTCATACTCTTCCTTTTTCAATATTATTGAAGCATTTATCAGGGTTATT
GTCTCATGAGCGGATACATATTTGAATGTATTTAGAAAAATAAACAAATAGGGGTTCCGCGC
ACATTTCCCCGAAAAGTGCCACCTGACGTCTAAGAAACCATTATTATCATGACATTAACCTA
TAAAAATAGGCGTATCACGAGGCCCTTTCGTCTTCAAGAA
```

TABLE 2 pHEBO-DR-LUC

Features:
Identification in record book: RF202-15
Cloning: DR-LUC cloned as BamHI+BglII 4.54 kb fragment into BAMHI of pHEBO.
Total bases: 11,616
Restriction Enzyme Intersections: Position:

| | |
|---|---|
| BamHI/BglII (Sau3A) | 1 |
| HindIII | 1,964 |
| EcoRI | 2,580 |
| BamHI | 4,547 |
| EcoRI | 8,556 |
| EcoRI | 8,953 |
| EcoRI | 11,239 |
| HindIII | 11,270 |

| Regions: | Positions: |
|---|---|
| DR (of EBV) | 1–1,963 |
| Luciferase (LUC) | 1,972–3,689 |
| part of SV40 | 3,701–4,546 |
| EBV-oriP (of EBV) | 4,979–7,159 |
| hygromycin resistance gene | 9,044–7,159 |
| ampicillin res. gene (AMP) (of pBR322) | 10,994–10,144 |

Sequence (SEQ ID NO: 2):
GATCTCTAGAACTGGATACTCGTGGGGGGTAAAGAAGGTGAATAAAAATTACAAACATTCTC
TGCCCAGCCTTCAGACTATCAAACCTAGATAATCATTCTATAAATAACCCAGGGCTTGCATC
ACAATTTAAAGGGAAGTTAAGATGGGGGATTACCTTCTAAGAGGAAATGACAAGCCACAGAC
ATCCCCACATATAGCCGGGTGTCCACTGTCTAATGTCAGTAATTTAATTCCATAGTGAAAAT
AGCACCCCCAACTCAATTTGGAATCCAGAAACTATATTGCACACCAACACCCCCTCCTCTGC
ACATGAGCAAGACAAGACATCTATGTTTATCTCTAAATGTGCCATGGAACCCGGTTGCCCAT
GCAGTGGTGTCAGACAGGAAAATGGTTAATTAACCACATCTTAAATTGCCACCTTAGGCAAA
TTGAAAATAGGCAGGCTGAAGAATTGCACAATACCCTAAACAGGTAAGAGGAATTAGTGACA
TTTTATGAATTTTTTTACAAACTTTCACACTCAAGAATAGAAACCCAATACCAACAGGTGTG
CAGGTGTGCATGACAAATCTTGGGGGTCTCAGAACCCAGGACCAGACTTTGAAGTCTCAGGT
ATAGGTCCTGGCTGAGATTCTATTAATAAAACAAGAGAGAAAGAAGGCGGGCGCCCATTAGA
ATCTGCTCGGCTGCCAGTAAGTTGCCAGCAAACAGGAACACAAACAAACCAAGGGTGTTGGC
CCCTACAGGCTCCCAAGGCGGGGGTTGGGCACAGGGCCAAGCTCTGCCACCACAGGAGGCAA
GTAGACATGCAGGAACACATGGCCCTGGCTAGGAAAGGGAGGAAATAGAGGCCACAGCCAAA
GTTAGGCTGCCGCCCCACCTGTGTACCCAGGGTGAGAGACCTTGGGAGGTCGTCAGCTTAAC
CAGCGCCGCCCTCACCCCATTGCCAACTTCCGGCTCACACAAAACCACTCCCAAAAATTGAA
GACTGGCCAAAATCCAGCTTCCGTCCCCGGGACGTGGTGCTTCCTAAAGGCGGGGCTCATGG
ATTAGCAGGGGCTTAGTGTGTCATGGTGAGGCAGGCAAGGCGAGCAACGGGGGCTTAGTGGC
TCAAAGTGATGCATCCCAAAGGCAGCCACCACGCTGGAGGGACATTGTCCACGGGACAAGGC
ACAGGCCAGGTCATGACCCAGGAAGTGGCGAGCATCGGTCAGCTGACCAAATGTGCAAAGGT
GACAAGTCAGTAAGGCACGCGGGGGGCCACGTCACCCCGGGGTGCTGGGGTGGGGATGGGC
TCAGGCAACCGTAAGGGAGGGGGGGGTAGGGGGGGAGGGATTACACTATAGGGTTCCCTTC
CTCTAGGTTCTATATACCTATAGGTATATACCCAGCTGCAATACCCTATTCCACCACTAGGT
TAATAACCTATAGGTTATTCTACCATTAAAAACGGAAGGAGGAAGGGTGGCGCACCTTAAGGT
AGGGTAGGGGGGTACCCCAGTAGGAACCTAGCTGAATCCTACCTAGCTCCACCCACCTGGTA
TATAGGGGCGGAGCTTAGGATACCTCCAGGATAATGGAACCCTATGGAGACCTACCTCTAGG
CTCCACCCACTAGGTATATCGGGGCGGAGCCCACTCCTGGTTCAACCCTATGG
AGGGGACCCTCCTGAGGCTCCGCCTACCCCAAATCTCGCGGGCCTCTAGCCCCTCCTCCTCT
CGTTATCCCAATAGAATGACCTCCAGGTACCACCCACCTGGTTACACACCTTAATGTAACCC
AACGGGCTAAAATCACACACCTGAATTAACCAATGAGAAGCCCCCCACACCTGAGCAAACCT
TAAGGTATTGCACAGAAACCCCAAAAAGAGGATAAAAGAAGGCGAGCTGGCCCGGCTCGCCA
GCGTCGTCCAGACGCTCGGGGGGTGCACACCTCCCAGCCGCAAGCTTGGCATTCCGGTACTG
TTGGTAAAATGGAAGACGCCAAAAACATAAAGAAAGGCCCGGCGCCATTCTATCCTCTAGAG
GATGGAACCGCTGGAGAGCAACTGCATAAGGCTATGAAGAGATACGCCCTGGTTCCTGGAAC
AATTGCTTTTACAGATGCACATATCGAGGTGAACATCACGTACGCGGAATACTTCGAAATGT
CCGTTCGGTTGGCAGAAGCTATGAAACGATATGGGCTGAATACAAATCACAGAATCGTCGTA
TGCAGTGAAAACTCTCTTCAATTCTTTATGCCGGTGTTGGGCGCGTTATTTATCGGAGTTGC
AGTTGCGCCCGCGAACGACATTTATAATGAACGTGAATTGCTCAACAGTATGAACATTTCGC
AGCCTACCGTAGTGTTTGTTTCCAAAAAGGGGTTGCAAAAAATTTTGAACGTGCAAAAAAAA
TTACCAATAATCCAGAAAATTATTATCATGGATTCTAAAACGGATTACCAGGGATTTCAGTC
GATGTACACGTTCGTCACATCTCATCTACCTCCCGGTTTTAATGAATACGATTTTGTACCAG
AGTCCTTTGATCGTGACAAAACAATTGCACTGATAATGAATTCCTCTGGATCTACTGGGTTA
CCTAAGGGTGTGGCCCTTCCGCATAGAACTGCCTGCGTCAGATTCTCGCATGCCAGAGATCC
TATTTTTGGCAATCAAATCATTCCGGATACTGCGATTTTAAGTGTTGTTCCATTCCATCACG
GTTTTGGAATGTTTACTACACTCGGATATTTGATATGTGGATTTCGAGTCGTCTTAATGTAT
AGATTTGAAGAAGAGCTGTTTTTACGATCCCTTCAGGATTACAAAATTCAAAGTGCGTTGCT
AGTACCAACCCTATTTTCATTCTTCGCCAAAAGCACTCTGATTGACAAATACGATTTATCTA
ATTTACACGAAATTGCTTCTGGGGGCGCACCTCTTTCGAAAGAAGTCGGGGAATCGGTTGCA
AAACGCTTCCATCTTCCAGGGATACGACAAGGATATGGGCTCACTGAGACTACATCAGCTAT
TCTGATTACACCCGAGGGGGATGATAAACCGGGCGCGGTCGGTAAAGTTGTTCCATTTTTTG
AAGCGAAGGTTGTGGATCTGGATACCGGGAAAACGCTGGGCGTTAATCAGAGAGGCGAATTA

TABLE 2-continued pHEBO-DR-LUC

```
TGTGTCAGAGGACCTATGATTATGTCCGGTTATGTAAACAATCCGGAAGCGACCAACGCCTT
GATTGACAAGGATGGATGGCTACATTCTGGAGACATAGCTTACTGGGACGAAGACGAACACT
TCTTCATAGTTGACCGCTTGAAGTCTTTAATTAAATACAAAGGATATCAGGTGGCCCCCGCT
GAATTGGAATCGATATTGTTACAACACCCCAACATCTTCGACGCGGGCGTGGCAGGTCTTCC
CGACGATGACGCCGGTGAACTTCCCGCCGCCGTTGTTGTTTTGGAGCACGGAAAGACGATGA
CGGAAAAAGAGATCGTGGATTACGTCGCCAGTCAAGTAACAACCGCGAAAAAGTTGCGCGGA
GGAGTTGTGTTTGTGGACGAAGTACCGAAAGGTCTTACCGGAAAACTCGACGCAAGAAAAAT
CAGAGAGATCCTCATAAAGGCCAAGAAGGGCGGAAAGTCCAAATTGTAAAATGTAACTGTAT
TCAGCGATGACGAAATTCTTAGCTATTGTAATGACTCTAGAGGATCTTTGTGAAGGAACCTT
ACTTCTGTGGTGTGACATAATTGGACAAACTACCTACAGAGATTTAAAGCTCTAAGGTAAAT
ATAAAATTTTTAAGTGTATAATGTGTTAAACTACTGATTCTAATTGTTTGTGTATTTTAGAT
TCCAACCTATGGAACTGATGAATGGGAGCAGTGGTGGAATGCCTTTAATGAGGAAAACCTGT
TTTGCTCAGAAGAAATGCCATCTAGTGATGATGAGGCTACTGCTGACTCTCAACATTCTACT
CCTCCAAAAAAGAAGAGAAAGGTAGAAGACCCCAAGGACTTTCCTTCAGAATTGCTAAGTTT
TTTGAGTCATGCTGTGTTTAGTAATAGAACTCTTGCTTGCTTTGCTATTTACACCACAAAGG
AAAAAGCTGCACTGCTATACAAGAAAATTATGGAAAAATATTCTGTAACCTTTATAAGTAGG
CATAACAGTTATAATCATAACATACTGTTTTTTCTTACTCCACACAGGCATAGAGTGTCTGC
TATTAATAACTATGCTCAAAAATTGTGTACCTTTAGCTTTTTAATTTGTAAAGGGGTTAATA
AGGAATATTTGATGTATAGTGCCTTGACTAGAGATCATAATCAGCCATACCACATTTGTAGA
GGTTTTACTTGCTTTAAAAAAACCTCCCACACCTCCCCCTGAACCTGAAACATAAAATGAATG
CAATTGTTGTTGTTAACTTGTTTATTGCAGCTTATAATGGTTACAAATAAAGCAATAGCATC
ACAAATTTCACAAATAAAGCATTTTTTTCACTGCATTCTAGTTGTGGTTTGTCCAAACTCAT
CAATGTATCTTATCATGTCTGGATCCTCTACGCCGGACGCATCGTGGCCGGCATCACCGGCG
CCACAGGTGCGGTTGCTGGCGCCTATATCGCCGACATCACCGATGGGGAAGATCGGGCTCGC
CACTTCGGGCTCATGAGCGCTTGTTTCGGCGTGGGTATGGTGGCAGGCCCCGTGGCCGGGGG
ACTGTTGGGCGCCATCTCCTTGCATGCACCATTCCTTGCGGCGGCGGTGCTCAACGGCCTCA
ACCTACTACTGGGCTGCTTCCTAATGCAGGAGTCGCATAAGGGAGAGCGTCGACTACGCGAT
CATGGCGACCACACCCGTCTCGACCGATGCCCTTGAGAGCCTTCAACCCAGTCAGCTCCTTC
CGGTGGGCGCGGGGCATGACTATCGTCGCCGCACTTATGACTGTCTTCTTTATCATGCAACT
CGTAGGACAGGTGCCCTGGCCGGGGTCCCGCGGAAACTCGGCCGTGGTGACAGGAAAAGGAC
AAGCAGCGAAAATTCACGCCCCCTTGGGAGGTGGCGGCATATGCAAAGGATAGCACTCCCAC
TCTACTACTGGGTATCATATGCTGACTGTATATGCATGAGGATAGCATATGCTACCCGGATA
CAGATTAGGATAGCATATACTACCCAGATATAGATTAGGATAGCATATGCTACCCAGATATA
GATTAGGATAGCCTATGCTACCCAGATATAAATTAGGATAGCATATACTACCCAGATATAGA
TTAGGATAGCATATGCTACCCAGATATAGATTAGGATAGCCTATGCTACCCAGATATAGATT
AGGATAGCATATGCTACCCAGATATAGATTAGGATAGCATATGCTATCCAGATATTTGGGTA
GTATATGCTACCCAGATATAAATTAGGATAGCATATACTACCCTAATCTCTATTAGGATAGC
ATATGCTACCCGGATACAGATTAGGATAGCATATACTACCCAGATATAGATTAGGATAGCAT
ATGCTACCCAGATATAGATTAGGATAGCCTATGCTACCCAGATATAAATTAGGATAGCATAT
ACTACCCAGATATAGATTAGGATAGCATATGCTACCCAGATATAGATTAGGATAGCCTATGC
TACCCAGATATAGATTAGGATAGCATATGCTATCCAGATATTTGGGTAGTATATGCTACCCA
TGGCAACATTAGCCCACCGTGCTCTCAGCGACCTCGTGAATATGAGGACCAACAACCCTGTG
CTTGGCGCTCAGGCGCAAGTGTGTGTAATTTGTCCTCCAGATCGCAGCAATCGCGCCCCTAT
CTTGGCCCGCCCACCTACTTATGCAGGTATTCCCCGGGGTGCCATTAGTGGTTTGTGGGCA
AGTGGTTTGACCGCAGTGGTTAGCGGGGTTACAATCAGCCAAGTTATTACACCCTTATTTTA
CAGTCCAAAACCGCAGGGCGGCGTGTGGGGGCTGACGCGTGCCCCCACTCCACAATTTCAAA
AAAAAGAGTGGCCACTTGTCTTTGTTTATGGGCCCCATTGGCGTGGAGCCCCGTTTAATTTT
CGGGGGTGTTAGAGACAACCAGTGGAGTCCGCTGCTGTCGGCGTCCACTCTCTTTCCCCTTG
TTACAAATAGAGTGTAACAACATGGTTCACCTGTCTTGGTCCCTGCCTGGGACACATCTTAA
TAACCCCAGTATCATATTGCACTAGGATTATGTGTTGCCCATAGCCATAAATTCGTGTGAGA
TGGACATCCAGTCTTTACGGCTTGTCCCCACCCCATGGATTTCTATTGTTAAAGATATTCAG
AATGTTTCATTCCTACACTAGTATTTATTGCCCAAGGGGTTTGTGAGGGTTATATTGGTGTC
ATAGCACAATGCCACCACTGAACCCCCCGTCCAAATTTTATTCTGGGGGCGTCACCTGAAAC
CTTGTTTTCGAGCACCTCACATACACCTTACTGTTCACAACTCAGCAGTTATTCTATTAGCT
AAACGAAGGAGAATGAAGAAGCAGGCGAAGATTCAGGAGAGTTCACTGCCCGCTCCTTGATC
TTCAGCCACTGCCCTTGTGACTAAAATGGTTCACTACCCTCGTGGAATCCTGACCCCATGTA
AATAAAACCGTGACAGCTCATGGGGTGGGAGATATCGCTGTTCCTTAGGACCCTTTTACTAA
CCCTAATTCGATAGCATATGCTTCCCGTTGGGTAACATATGCTATTGAATTAGGGTTAGTCT
GGATAGTATATACTACTACCCGGGAAGCATATGCTACCCGTTTAGGGTTAACAAGGGGCCT
TATAAACACTATTGCTAATGCCCTCTTGAGGGTCCGCTTATCGGTAGCTACACAGGCCCCTC
TGATTGACGTTGGTGTAGCCTCCCGTAGTCTTCCTGGGCCCCTGGGAGGTACATGTCCCCCA
GCATTGGTGTAAGAGCTTCAGCCAAGAGTTACACATAAAGGCAATGTTGTGTTGCAGTCCAC
AGACTGCAAAGTCTGCTCCAGGATGAAAGCCACTCAGTGTTGGCAAATGTGCACATCCATTT
ATAAGGATGTCAACTACAGTCAGAGAACCCCTTTGTGTTTGGTCCCCCCCCGTGTCACATGT
GGAACAGGGCCCAGTTGGCAAGTTGTACCAACCAACTGAAGGGATTACATGCACTGCCCCGT
GACCAATACAAAACAAAAGCGCTCCTCGTACCAGCGAAGAAGGGGCAGAGATGCCGTAGTCA
GGTTTAGTTCGTCCGGCGGCGCCAGAAATCCGCGCGGTGGTTTTTGGGGGTCGGGGGTGTTT
GGCAGCCACAGACGCCCGGTGTTCGTGTCGCGCCAGTACATGCGGTCCATGCCCAGGCCATC
CAAAAACCATGGGTCTGTCTGCTCAGTCCAGTCGTGGACCTGACCCCACGCAACGCCCAAAA
GAATAACCCCCACGAACCATAAACCATTCCCCATGGGGGACCCCGTCCCTAACCCACGGGGC
CCGTGGCTATGGCGGGCTTGCCGCCCCGACGTTGGCTGCGAGCCCTGGGCCTTCACCCGAAC
TTGGGGGTTGGGGTGGGGAAAAGGAAGAAACGCGGGCGTATTGGCCCCAATGGGGTCTCGGT
GGGGTATCGACAGAGTGCCAGCCCTGGGACCGAACCCCGCGTTTATGAACAAACGACCCAAC
ACCCGTGCGTTTATTCTGTCTTTTTATTGCCGTCATAGCGCGGGTTCCTTCCGGTATTGTC
TCCTTCCGTGTTTCAGTTAGCCTCCCCCATCTCCCGATCCCCTCGGACGAGTGCTGGGGCGT
CGGTTTCCACTATCGGCGAGTACTTCTACACAGCCATCGGTCCAGACGGCCGCGCTTCTGCG
GGCGATTTGTGTACGCCCGACAGTCCCGGCTCCGGATCGGACGATTGCGTCGCATCGACCCT
```

TABLE 2-continued pHEBO-DR-LUC

```
GCGCCCAAGCTGCATCATCGAAATTGCCGTCAACCAAGCTCTGATAGAGTTGGTCAAGACCA
ATGCGGAGCATATACGCCCGGAGCCGCGGCGATCCTGCAAGCTCCGGATGCCTCCGCTCGAA
GTAGCGCGTCTGCTGCTCCATACAAGCCAACCACGGCCTCCAGAAGAAGATGTTGGCGACCT
CGTATTGGGAATCCCCGAACATCGCCTCGCTCCAGTCAATGACCGCTGTTATGCGGCCATTG
TCCGTCAGGACATTGTTGGAGCCGAAATCCGCGTGCACGAGGTGCCGGACTTCGGGGCAGTC
CTCGGCCCAAAGCATCAGCTCATCGAGAGCCTGCGCGACGGACGCACTGACGGTGTCGTCCA
TCACAGTTTGCCAGTGATACACATGGGGATCAGCAATCGCGCATATGAAATCACGCCATGTA
GTGTATTGACCGATTCCTTGCGGTCCGAATGGGCCGAACCCGCTCGTCTGGCTAAGATCGGC
CGCAGCGATCGCATCCATGGCCTCCGCGACCGGCTGCAGAACAGCGGGCAGTTCGGTTTCAG
GCAGGTCTTGCAACGTGACACCCTGTGCACGGCGGGAGATGCAATAGGTCAGGCTCTCGCTG
AATTCCCCAATGTCAAGCACTTCCGGAATCGGGAGCGCGGCCGATGCAAAGTGCCGATAAAC
ATAACGATCTTTGTAGAAACCATCGGCGCAGCTATTTACCCGCAGGACATATCCACGCCCTC
CTACATCGAAGCTGAAAGCACGAGATTCTTCGCCCTCCGAGAGCTGCATCAGGTCGGAGACG
CTGTCGAACTTTTCGATCAGAAACTTCTCGACAGACGTCGCGGTGAGTTCAGGCTTTTTCAT
ATCTCATTGCCCCCGGGGGATCTGCGGCACGCTGTTGACGCTGTTAAGCGGGTCGCTGCAGG
GTCGCTCGGTGTTCGAGGCCACACGCGTCACCTTAATATGCGAAGTGGACCTGGGACCGCGC
CGCCCCGACTGCATCTGCGTGTTCGAATTCGCCAATGACAAGACGCTGGGCGGGGTTTGTGT
CATCATAGAACTAAAGACATGCAAATATATTTCTTCCGGGGACACCGCCAGCAAACGCGAGC
AACGGGCCACGGGGATGAAGCAGGGCGGCACCTCGCTAACGGATTCACCACTCCAAGAATTG
GAGCCAATCAATTCTTGCGGAGAACTGTGAATGCGCAAACCAACCCTTGGCAGAACATATCC
ATCGCGTCCGCCATCTCCAGCAGCCGCACGCGGCGCATCTCGGGCAGGCCGACGCGCTGGGC
TACGTCTTGCTGGCGTTCGCGACGCGAGGCTGGATGGCCTTCCCCATTATGATTCTTCTCGC
TTCCGGCGGCATCGGGATGCCCGCGTTGCAGGCCATGCTGTCCAGGCAGGTAGATGACGACC
ATCAGGGCAGCAAAAGGCCAGGAACCGTAAAAAGGCCGCGTTGCTGGCGTTTTTCCATAGGC
TCCGCCCCCTGACGAGCATCACAAAAATCGACGCTCAAGTCAGAGGTGGCGAAACCCGACA
GGACTATAAAGATACCAGGCGTTTCCCCCTGGAAGCTCCCTCGTGCGCTCTCCTGTTCCGAC
CCTGCCGCTTACCGGATACCTGTCCGCCTTTCTCCCTTCGGGAAGCGTGGCGCTTTCTCAAT
GCTCACGCTGTAGGTATCTCAGTTCGGTGTAGGTCGTTCGCTCCAAGCTGGGCTGTGTGCAC
GAACCCCCCGTTCAGCCCGACCGCTGCGCCTTATCCGGTAACTATCGTCTTGAGTCCAACCC
GGTAAGACACGACTTATCGCCACTGGCAGCAGCCACTGGTAACAGGATTAGCAGAGCGAGGT
ATGTAGGCGGTGCTACAGAGTTCTTGAAGTGGTGGCCTAACTACGGCTACACTAGAAGGACA
GTATTTGGTATCTGCGCTCTGCTGAAGCCAGTTACCTTCGGAAAAAGAGTTGGTAGCTCTTG
ATCCGGCAAACAAACCACCGCTGGTAGCGGTGGTTTTTTTGTTTGCAAGCAGCAGATTACGC
GCAGAAAAAAAGGATCTCAAGAAGATCCTTTGATCTTTTCTACGGGGTCTGACGCTCAGTGG
AACGAAAACTCACGTTAAGGGATTTTGGTCATGAGATTATCAAAAAGGATCTTCACCTAGAT
CCTTTTAAATTAAAAATGAAGTTTTAAATCAATCTAAAGTATATATGAGTAAACTTGGTCTG
ACAGTTACCAATGCTTAATCAGTGAGGCACCTATCTCAGCGATCTGTCTATTTCGTTCATCC
ATAGTTGCCTGACTCCCCGTCGTGTAGATAACTACGATACGGGAGGGCTTACCATCTGGCCC
CAGTGCTGCAATGATACCGCGAGACCCACGCTCACCGGCTCCAGATTTATCAGCAATAAACC
AGCCAGCCGGAAGGGCCGAGCGCAGAAGTGGTCCTGCAACTTTATCCGCCTCCATCCAGTCT
ATTAATTGTTGCCGGGAAGCTAGAGTAAGTAGTTCGCCAGTTAATAGTTTGCGCAACGTTGT
TGCCATTGCTGCAGGCATCGTGGTGTCACGCTCGTCGTTTGGTATGGCTTCATTCAGCTCCG
GTTCCCAACGATCAAGGCGAGTTACATGATCCCCCATGTTGTGCAAAAAAGCGGTTAGCTCC
TTCGGTCCTCCGATCGTTGTCAGAAGTAAGTTGGCCGCAGTGTTATCACTCATGGTTATGGC
AGCACTGCATAATTCTCTTACTGTCATGCCATCCGTAAGATGCTTTTCTGTGACTGGTGAGT
ACTCAACCAAGTCATTCTGAGAATAGTGTATGCGGCGACCGAGTTGCTCTTGCCCGGCGTCA
ACACGGGATAATACCGCGCCACATAGCAGAACTTTAAAAGTGCTCATCATTGGAAAACGTTC
TTCGGGGCGAAAACTCTCAAGGATCTTACCGCTGTTGAGATCCAGTTCGATGTAACCCACTC
GTGCACCCAACTGATCTTCAGCATCTTTTACTTTCACCAGCGTTTCTGGGTGAGCAAAAACA
GGAAGGCAAAATGCCGCAAAAAAGGGAATAAGGGCGACACGGAAATGTTGAATACTCATACT
CTTCCTTTTTCAATATTATTGAAGCATTTATCAGGGTTATTGTCTCATGAGCGGATACATAT
TTGAATGTATTTAGAAAAATAAACAAATAGGGGTTCCGCGCACATTTCCCCGAAAAGTGCCA
CCTGACGTCTAAGAAACCATTATTATCATGACATTAACCTATAAAAATAGGCGTATCACGAG
GCCCTTTCGTCTTCAAGAATTCTCATGTTTGACAGCTTATCATCGATAAGCTTTAATGCGGT
AGTTTATCACAGTTAAATTGCTAACGCAGTCAGGCACCGTGTATGAAATCTAACAATGCGCT
CATCGTCATCCTCGGCACCGTCACCCTGGATGCTGTAGGCATAGGCTTGGTTATGCCGGTAC
TGCCGGGCCTCTTGCGGGATATCGTCCATTCCGACAGCATCGCCAGTCACTATGGCGTGCTG
CTAGCGCTATATGCGTTGATGCAATTTCTATGCGCACCCGTTCTCGGAGCACTGTCCGACCG
CTTTGGCCGCCGCCCAGTCCTGCTCGCTTCGCTACTTGGAGCCACTATCGACTACGCGATCA
TGGCGACCACACCCGTCCTGTG
```

---

We claim:

1. A method for the in vitro detection of tumor promoters, comprising the following steps:
   (a) contacting EBV-containing cells which contain pHEBO-DR-CAT or pHEBO-DR-LUC with the substance to be examined;
   (b) incubating the cells in contact with the substance to be examined in a $CO_2$-containing atmosphere at 37° C. for approximately one to three days;
   (c) determining the quantity of the expressed reporter gene product; and
   (d) comparing the quantity of the expressed reporter gene to the quantity of the expressed reporter gene from untreated cells.

2. A DNA construct comprising:
   (a) the control region for the activation of the Epstein-Barr virus (EBV) DR gene;
   (b) the episomal origin of replication of EBV (oriP)
   (c) a reporter gene;
   (d) a resistance gene R1 for the selection of transfected eukaryotic cells; and
   (e) a resistance gene R2 for selection in procaryotic cells.

3. A DNA construct according to claim 2 wherein R2 is an ampicillin resistance gene.

4. A DNA construct according to claim 2, wherein the reporter gene is chloramphenicol acetyltransferase (CAT).

5. A DNA construct according to claim 2 wherein the reporter gene is firefly luciferase (LUC).

6. A DNA construct according to claim 2 wherein R1 is a hygromycin resistance gene.

7. An in-vitro test for the detection of tumor promoters, comprising the following method steps:
   (a) EBV-containing cells containing a DNA construct according to claim 2 are brought in contact with the substance to be examined;
   (b) the cells in contact with the substance to be examined are kept in a $CO_2$-containing atmosphere at 37° C. for approximately one to three days; and
   (c) the quantity of the product expressed from the reporter gene is determined.

8. The in-vitro test according to claim 7, wherein Raji cells are employed as the EBV-containing cells.

9. The in-vitro test according to claim 7, wherein the reporter gene is chloramphenicol acetyltransferase (CAT).

10. The in-vitro test according to claim 7, wherein the reporter gene is firefly luciferase (LUC).

11. The in-vitro test according to claim 9, wherein the number of EBV-containing cells containing the DNA construct is from 1 to $5 \times 10^6$ per experiment.

12. The in-vitro test according to claim 10, wherein the number of EBV-containing cells containing the DNA construct is from 0.1 to $1.0 \times 10^4$ cells per experiment.

13. The in-vitro test according to claim 7, comprising the additional step of:
   (d) the quantity of the product expressed from the reporter gene is compared to the quantity of the product expressed from the reporter gene from untreated cells.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 10580 base pairs (B) TYPE: nucleic acid
(C) STRANDEDNESS: double
(D) TOPOLOGY: circular (ii) MOLECULE TYPE: DNA (genomic)

(iii) HYPOTHETICAL: NO (iv) ANTI-SENSE: NO (x) PUBLICATION INFORMATION:
(H) DOCUMENT NUMBER: WO PCT/DE91/00652
(I) FILING DATE: 16-AUG-1991
(J) PUBLICATION DATE: 04-MAR-1993

(xi) SEQUENCE DESCRIPTION: SEQ ID NO:1:

| | | | | | | |
|---|---|---|---|---|---|---|
| TTCTCATGTT | TGACAGCTTA | TCATCGATAA | GCTTTAATGC | GGTAGTTTAT | CACAGTTAAA | 60 |
| TTGCTAACGC | AGTCAGGCAC | CGTGTATGAA | ATCAACAAT | GCGCTCATCG | TCATCCTCGG | 120 |
| CACCGTCACC | CTGGATGCTG | TAGGCATAGG | CTTGGTTATG | CCGGTACTGC | CGGGCCTCTT | 180 |
| GCGGGATATC | GTCCATTCCG | ACAGCATCGC | CAGTCACTAT | GGCGTGCTGC | TAGCGCTATA | 240 |
| TGCGTTGATG | CAATTTCTAT | GCGCACCCGT | TCTCGGAGCA | CTGTCCGACC | GCTTTGGCCG | 300 |
| CCGCCCAGTC | CTGCTCGCTT | CGCTACTTGG | AGCCACTATC | GACTACGCGA | TCATGGCGAC | 360 |
| CACACCCGTC | CTGTGGATCC | TCTACGCCGG | ACGCATCGTG | GCCGGCATCA | CCGGCGCCAC | 420 |
| AGGTGCGGTT | GCTGGCGCCT | ATATCGCCGA | CATCACCGAT | GGGGAAGATC | GGGCTCGCCA | 480 |
| CTTCGGGCTC | ATGAGCGCTT | GTTTCGGCGT | GGGTATGGTG | CAGGCCCCG | TGCCGGGGG | 540 |
| ACTGTTGGGC | GCCATCTCCT | TGCATGCCTG | CAGGTCGACT | CTAGAACTGG | ATACTCGTGG | 600 |
| GGGGTAAAGA | AGGTGAATAA | AAATTACAAA | CATTCTCTGC | CCAGCCTTCA | GACTATCAAA | 660 |
| CCTAGATAAT | CATTCTATAA | ATAACCCAGG | GCTTGCATCA | CAATTTAAAG | GAAGTTAAG | 720 |
| ATGGGGATT | ACCTTCTAAG | AGGAAATGAC | AAGCCACAGA | CATCCCCACA | TATAGCCGGG | 780 |
| TGTCCACTGT | CTAATGTCAG | TAATTTAATT | CCATAGTGAA | AATAGCACCC | CCAACTCAAT | 840 |
| TTGGAATCCA | GAAACTATAT | TGCACACCAA | CACCCCCTCC | TCTGCACATG | AGCAAGACAA | 900 |
| GACATCTATG | TTTATCTCTA | AATGTGCCAT | GGAACCCGGT | TGCCCATGCA | GTGGTGTCAG | 960 |
| ACAGGAAAAT | GGTTAATTAA | CCACATCTTA | AATTGCCACC | TTAGGCAAAT | TGAAAATAGG | 1020 |
| CAGGCTGAAG | AATTGCACAA | TACCCTAAAC | AGGTAAGAGG | AATTAGTGAC | ATTTTATGAA | 1080 |
| TTTTTTTACA | AACTTTCACA | CTCAAGAATA | GAAACCCAAT | ACCAACAGGT | GTGCAGGTGT | 1140 |
| GCATGACAAA | TCTTGGGGGT | CTCAGAACCC | AGGACCAGAC | TTTGAAGTCT | CAGGTATAGG | 1200 |
| TCCTGGCTGA | GATTCTATTA | ATAAACAAG | AGAGAAAGAA | GGCGGGCGCC | CATTAGAATC | 1260 |
| TGCTCGGCTG | CCAGTAAGTT | GCCAGCAAAC | AGGAACACAA | ACAAACCAAG | GGTGTTGGCC | 1320 |
| CCTACAGGCT | CCCAAGGCGG | GGGTTGGGCA | CAGGGCCAAG | CTCTGCCACC | ACAGGAGGCA | 1380 |
| AGTAGACATG | CAGGAACACA | TGGCCCTGGC | TAGGAAAGGG | AGGAAATAGA | GGCCACAGCC | 1440 |
| AAAGTTAGGC | TGCCGCCCCA | CCTGTGTACC | CAGGGTGAGA | GACCTTGGGA | GGTCGTCAGC | 1500 |
| TTAACCAGCG | CCGCCCTCAC | CCCATTGCCA | ACTTCCGGCT | CACACAAAAC | CACTCCCAAA | 1560 |
| AATTGAAGAC | TGGCCAAAAT | CCAGCTTCCG | TCCCGGGAC | GTGGTGCTTC | CTAAAGGCGG | 1620 |
| GGCTCATGGA | TTAGCAGGGG | CTTAGTGTGT | CATGGTGAGG | CAGGCAAGGC | GAGCAACGGG | 1680 |
| GGCTTAGTGG | CTCAAAGTGA | TGCATCCCAA | AGGCAGCCAC | CACGCTGGAG | GGACATTGTC | 1740 |
| CACGGGACAA | GGCACAGGCC | AGGTCATGAC | CCAGGAAGTG | GCGAGCATCG | GTCAGCTGAC | 1800 |
| CAAATGTGCA | AAGGTGACAA | GTCAGTAAGG | CACGCGGGGG | GCCACGTCAC | CCCGGGGTGC | 1860 |
| TGGGGTGGGG | GATGGGCTCA | GGCAACCGTA | AGGGAGGGGG | GGGTAGGGGG | GGGAGGGATT | 1920 |

| | | | | | | |
|---|---|---|---|---|---|---|
| ACACTATAGG | GTTCCCTTCC | TCTAGGTTCT | ATATACCTAT | AGGTATATAC | CCAGCTGCAA | 1980 |
| TACCCTATTC | CACCACTAGG | TTAATAACCT | ATAGGTTATT | CTACCATTAA | AACGGAAGGA | 2040 |
| GGAAGGGTGG | CGCACCTTAA | GGTAGGGTAG | GGGGGTACCC | CAGTAGGAAC | CTAGCTGAAT | 2100 |
| CCTACCTAGC | TCCACCCACC | TGGTATATAG | GGGCGGAGCT | TAGGATACCT | CCAGGATAAT | 2160 |
| GGAACCCTAT | GGAGACCTAC | CTCTAGGCTC | CACCCACTAG | GTATATCGGG | GCGGAGCCCA | 2220 |
| CTCCTCCCCC | TCCTGGTTCA | ACCCTATGGA | GGGGACCCTC | CTGAGGCTCC | GCCTACCCCA | 2280 |
| AATCTCGCGG | GCCTCTAGCC | CCTCCTCCTC | TCGTTATCCC | AATAGAATGA | CCTCCAGGTA | 2340 |
| CCACCCACCT | GGTTACACAC | CTTAATGTAA | CCCAACGGGC | TAAAATCACA | CACCTGAATT | 2400 |
| AACCAATGAG | AAGCCCCCCA | CACCTGAGCA | AACCTTAAGG | TATTGCACAG | AAACCCCAAA | 2460 |
| AAGAGGATAA | AAGAAGGCGA | GCTGGCCCGG | CTCGCCAGCG | TCGTCCAGAC | GCTCGGGGGG | 2520 |
| TGCACACCTC | CCAGCCGCAA | GCTTGGCGAG | ATTTTCAGGA | GCTAAGGAAG | CTAAAATGGA | 2580 |
| GAAAAAATC | ACTGGATATA | CCACCGTTGA | TATATCCCAA | TGGCATCGTA | AAGAACATTT | 2640 |
| TGAGGCATTT | CAGTCAGTTG | CTCAATGTAC | CTATAACCAG | ACCGTTCAGC | TGGATATTAC | 2700 |
| GGCCTTTTTA | AAGACCGTAA | AGAAAATAA | GCACAAGTTT | TATCCGGCCT | TTATTCACAT | 2760 |
| TCTTGCCCGC | CTGATGAATG | CTCATCCGGA | ATTCCGTATG | GCAATGAAAG | ACGGTGAGCT | 2820 |
| GGTGATATGG | GATAGTGTTC | ACCCTTGTTA | CACCGTTTTC | CATGAGCAAA | CTGAAACGTT | 2880 |
| TTCATCGCTC | TGGAGTGAAT | ACCACGACGA | TTTCCGGCAG | TTTCTACACA | TATATTCGCA | 2940 |
| AGATGTGGCG | TGTTACGGTG | AAAACCTGGC | CTATTTCCCT | AAAGGGTTTA | TTGAGAATAT | 3000 |
| GTTTTCGTC | TCAGCCAATC | CCTGGGTGAG | TTTCACCAGT | TTTGATTTAA | ACGTGGCCAA | 3060 |
| TATGGACAAC | TTCTTCGCCC | CCGTTTTCAC | CATGGGCAAA | TATTATACGC | AAGGCGACAA | 3120 |
| GGTGCTGATG | CCGCTGGCGA | TTCAGGTTCA | TCATGCCGTC | TGTGATGGCT | TCCATGTCGG | 3180 |
| CAGAATGCTT | AATGAATTAC | AACAGTACTG | CGATGAGTGG | CAGGGCGGGG | CGTAATTTTT | 3240 |
| TTAAGGCAGT | TATTGGTGCC | CTTAAACGCC | TGGTGCTACG | CCTGAATAAG | TGATAATAAG | 3300 |
| CGGATGAATG | GCAGAAATTC | GCCGGATCTT | TGTGAAGGAA | CCTTACTTCT | GTGGTGTGAC | 3360 |
| ATAATTGGAC | AAACTACCTA | CAGAGATTTA | AAGCTCTAAG | GTAAATATAA | AATTTTTAAG | 3420 |
| TGTATAATGT | GTTAAACTAC | TGATTCTAAT | TGTTTGTGTA | TTTTAGATTC | CAACCTATGG | 3480 |
| AACTGATGAA | TGGGAGCAGT | GGTGGAATGC | CTTTAATGAG | GAAAACCTGT | TTTGCTCAGA | 3540 |
| AGAAATGCCA | TCTAGTGATG | ATGAGGCTAC | TGCTGACTCT | CAACATTCTA | CTCCTCCAAA | 3600 |
| AAAGAAGAGA | AAGGTAGAAG | ACCCCAAGGA | CTTTCCTTCA | GAATTGCTAA | GTTTTTGAG | 3660 |
| TCATGCTGTG | TTTAGTAATA | GAACTCTTGC | TTGCTTTGCT | ATTTACACCA | CAAAGGAAAA | 3720 |
| AGCTGCACTG | CTATACAAGA | AAATTATGGA | AAAATATTCT | GTAACCTTTA | TAAGTAGGCA | 3780 |
| TAACAGTTAT | AATCATAACA | TACTGTTTTT | TCTTACTCCA | CACAGGCATA | GAGTGTCTGC | 3840 |
| TATTAATAAC | TATGCTCAAA | AATTGTGTAC | CTTTAGCTTT | TTAATTTGTA | AAGGGGTTAA | 3900 |
| TAAGGAATAT | TTGATGTATA | GTGCCTTGAC | TAGAGATCAT | AATCAGCCAT | ACCACATTTG | 3960 |
| TAGAGGTTTT | ACTTGCTTTA | AAAAACCTCC | CACACCTCCC | CCTGAACCTG | AAACATAAAA | 4020 |
| TGAATGCAAT | TGTTGTTGTT | AACTTGTTTA | TTGCAGCTTA | TAATGGTTAC | AAATAAAGCA | 4080 |
| ATAGCATCAC | AAATTTCACA | AATAAAGCAT | TTTTTCACT | GCATTCTAGT | TGTGGTTTGT | 4140 |
| CCAAACTCAT | CAATGTATCT | TATCATGTCT | GGATCCCCGG | GTACCGAGCT | CGCCTCGACC | 4200 |
| GATGCCCTTG | AGAGCCTTCA | ACCCAGTCAG | CTCCTTCCGG | TGGGCGCGGG | GCATGACTAT | 4260 |
| CGTCGCCGCA | CTTATGACTG | TCTTCTTTAT | CATGCAACTC | GTAGGACAGG | TGCCCTGGCC | 4320 |

| | | | | | | |
|---|---|---|---|---|---|---|
| GGGGTCCCGC | GGAAACTCGG | CCGTGGTGAC | AGGAAAAGGA | CAAGCAGCGA | AAATTCACGC | 4380 |
| CCCCTTGGGA | GGTGGCGGCA | TATGCAAAGG | ATAGCACTCC | CACTCTACTA | CTGGGTATCA | 4440 |
| TATGCTGACT | GTATATGCAT | GAGGATAGCA | TATGCTACCC | GGATACAGAT | TAGGATAGCA | 4500 |
| TATACTACCC | AGATATAGAT | TAGGATAGCA | TATGCTACCC | AGATATAGAT | TAGGATAGCC | 4560 |
| TATGCTACCC | AGATATAAAT | TAGGATAGCA | TATACTACCC | AGATATAGAT | TAGGATAGCA | 4620 |
| TATGCTACCC | AGATATAGAT | TAGGATAGCC | TATGCTACCC | AGATATAGAT | TAGGATAGCA | 4680 |
| TATGCTACCC | AGATATAGAT | TAGGATAGCA | TATGCTATCC | AGATATTGG | GTAGTATATG | 4740 |
| CTACCCAGAT | ATAAATTAGG | ATAGCATATA | CTACCTAAT | CTCTATTAGG | ATAGCATATG | 4800 |
| CTACCCGGAT | ACAGATTAGG | ATAGCATATA | CTACCCAGAT | ATAGATTAGG | ATAGCATATG | 4860 |
| CTACCCAGAT | ATAGATTAGG | ATAGCCTATG | CTACCCAGAT | ATAAATTAGG | ATAGCATATA | 4920 |
| CTACCCAGAT | ATAGATTAGG | ATAGCATATG | CTACCCAGAT | ATAGATTAGG | ATAGCCTATG | 4980 |
| CTACCCAGAT | ATAGATTAGG | ATAGCATATG | CTATCCAGAT | ATTGGGTAG | TATATGCTAC | 5040 |
| CCATGGCAAC | ATTAGCCCAC | CGTGCTCTCA | GCGACCTCGT | GAATATGAGG | ACCAACAACC | 5100 |
| CTGTGCTTGG | CGCTCAGGCG | CAAGTGTGTG | TAATTTGTCC | TCCAGATCGC | AGCAATCGCG | 5160 |
| CCCCTATCTT | GGCCCGCCCA | CCTACTTATG | CAGGTATTCC | CCGGGGTGCC | ATTAGTGGTT | 5220 |
| TTGTGGGCAA | GTGGTTTGAC | CGCAGTGGTT | AGCGGGGTTA | CAATCAGCCA | AGTTATTACA | 5280 |
| CCCTTATTTT | ACAGTCCAAA | ACCGCAGGGC | GGCGTGTGGG | GGCTGACGCG | TGCCCCACT | 5340 |
| CCACAATTTC | AAAAAAAGA | GTGGCCACTT | GTCTTTGTTT | ATGGGCCCCA | TTGGCGTGGA | 5400 |
| GCCCGTTTA | ATTTCGGGG | GTGTTAGAGA | CAACCAGTGG | AGTCCGCTGC | TGTCGGCGTC | 5460 |
| CACTCTCTTT | CCCCTTGTTA | CAAATAGAGT | GTAACAACAT | GGTTCACCTG | TCTTGGTCCC | 5520 |
| TGCCTGGGAC | ACATCTTAAT | AACCCCAGTA | TCATATTGCA | CTAGGATTAT | GTGTTGCCCA | 5580 |
| TAGCCATAAA | TTCGTGTGAG | ATGGACATCC | AGTCTTTACG | GCTTGTCCCC | ACCCCATGGA | 5640 |
| TTTCTATTGT | TAAAGATATT | CAGAATGTTT | CATTCCTACA | CTAGTATTTA | TTGCCCAAGG | 5700 |
| GGTTTGTGAG | GGTTATATTG | GTGTCATAGC | ACAATGCCAC | CACTGAACCC | CCCGTCCAAA | 5760 |
| TTTTATTCTG | GGGGCGTCAC | CTGAAACCTT | GTTTCGAGC | ACCTCACATA | CACCTTACTG | 5820 |
| TTCACAACTC | AGCAGTTATT | CTATTAGCTA | AACGAAGGAG | AATGAAGAAG | CAGGCGAAGA | 5880 |
| TTCAGGAGAG | TTCACTGCCC | GCTCCTTGAT | CTTCAGCCAC | TGCCCTTGTG | ACTAAAATGG | 5940 |
| TTCACTACCC | TCGTGGAATC | CTGACCCCAT | GTAAATAAAA | CCGTGACAGC | TCATGGGGTG | 6000 |
| GGAGATATCG | CTGTTCCTTA | GGACCCTTTT | ACTAACCCTA | ATTCGATAGC | ATATGCTTCC | 6060 |
| CGTTGGGTAA | CATATGCTAT | TGAATTAGGG | TTAGTCTGGA | TAGTATATAC | TACTACCCGG | 6120 |
| GAAGCATATG | CTACCCGTTT | AGGGTTAACA | AGGGGGCCTT | ATAAACACTA | TTGCTAATGC | 6180 |
| CCTCTTGAGG | GTCCGCTTAT | CGGTAGCTAC | ACAGGCCCCT | CTGATTGACG | TTGGTGTAGC | 6240 |
| CTCCGTAGT | CTTCCTGGGC | CCCTGGGAGG | TACATGTCCC | CCAGCATTGG | TGTAAGAGCT | 6300 |
| TCAGCCAAGA | GTTACACATA | AAGGCAATGT | TGTGTTGCAG | TCCACAGACT | GCAAAGTCTG | 6360 |
| CTCCAGGATG | AAAGCCACTC | AGTGTTGGCA | AATGTGCACA | TCCATTTATA | AGGATGTCAA | 6420 |
| CTACAGTCAG | AGAACCCCTT | TGTGTTTGGT | CCCCCCCGT | GTCACATGTG | AACAGGGCC | 6480 |
| CAGTTGGCAA | GTTGTACCAA | CCAACTGAAG | GGATTACATG | CACTGCCCCG | TGACCAATAC | 6540 |
| AAAACAAAAG | CGCTCCTCGT | ACCAGCGAAG | AAGGGGCAGA | GATGCCGTAG | TCAGGTTTAG | 6600 |
| TTCGTCCGGC | GGCGCCAGAA | ATCCGCGCGG | TGGTTTTTGG | GGGTCGGGGG | TGTTTGGCAG | 6660 |
| CCACAGACGC | CCGGTGTTCG | TGTCGCGCCA | GTACATGCGG | TCCATGCCCA | GGCCATCCAA | 6720 |

-continued

| | | | | | | |
|---|---|---|---|---|---|---|
| AAACCATGGG | TCTGTCTGCT | CAGTCCAGTC | GTGGACCTGA | CCCCACGCAA | CGCCCAAAAG | 6780 |
| AATAACCCCC | ACGAACCATA | AACCATTCCC | CATGGGGGAC | CCCGTCCCTA | ACCCACGGGG | 6840 |
| CCCGTGGCTA | TGGCGGGCTT | GCCGCCCCGA | CGTTGGCTGC | GAGCCCTGGG | CCTTCACCCG | 6900 |
| AACTTGGGGG | TTGGGGTGGG | GAAAAGGAAG | AAACGCGGGC | GTATTGGCCC | CAATGGGGTC | 6960 |
| TCGGTGGGGT | ATCGACAGAG | TGCCAGCCCT | GGGACCGAAC | CCGCGTTTA | TGAACAAACG | 7020 |
| ACCCAACACC | CGTGCGTTTT | ATTCTGTCTT | TTTATTGCCG | TCATAGCGCG | GGTTCCTTCC | 7080 |
| GGTATTGTCT | CCTTCCGTGT | TTCAGTTAGC | CTCCCCCATC | TCCCGATCCC | CTCGGACGAG | 7140 |
| TGCTGGGGCG | TCGGTTTCCA | CTATCGGCGA | GTACTTCTAC | ACAGCCATCG | GTCCAGACGG | 7200 |
| CCGCGCTTCT | GCGGGCGATT | TGTGTACGCC | CGACAGTCCC | GGCTCCGGAT | CGGACGATTG | 7260 |
| CGTCGCATCG | ACCCTGCGCC | AAGCTGCAT | CATCGAAATT | GCCGTCAACC | AAGCTCTGAT | 7320 |
| AGAGTTGGTC | AAGACCAATG | CGGAGCATAT | ACGCCCGGAG | CCGCGGCGAT | CCTGCAAGCT | 7380 |
| CCGGATGCCT | CCGCTCGAAG | TAGCGCGTCT | GCTGCTCCAT | ACAAGCCAAC | CACGGCCTCC | 7440 |
| AGAAGAAGAT | GTTGGCGACC | TCGTATTGGG | AATCCCCGAA | CATCGCCTCG | CTCCAGTCAA | 7500 |
| TGACCGCTGT | TATGCGGCCA | TTGTCCGTCA | GGACATTGTT | GGAGCCGAAA | TCCGCGTGCA | 7560 |
| CGAGGTGCCG | GACTTCGGGG | CAGTCCTCGG | CCCAAAGCAT | CAGCTCATCG | AGAGCCTGCG | 7620 |
| CGACGGACGC | ACTGACGGTG | TCGTCCATCA | CAGTTTGCCA | GTGATACACA | TGGGGATCAG | 7680 |
| CAATCGCGCA | TATGAAATCA | CGCCATGTAG | TGTATTGACC | GATTCCTTGC | GGTCCGAATG | 7740 |
| GGCCGAACCC | GCTCGTCTGG | CTAAGATCGG | CCGCAGCGAT | CGCATCCATG | GCCTCCGCGA | 7800 |
| CCGGCTGCAG | AACAGCGGGC | AGTTCGGTTT | CAGGCAGGTC | TTGCAACGTG | ACACCCTGTG | 7860 |
| CACGGCGGGA | GATGCAATAG | GTCAGGCTCT | CGCTGAATTC | CCCAATGTCA | AGCACTTCCG | 7920 |
| GAATCGGGAG | CGCGGCCGAT | GCAAGTGCC | GATAAACATA | ACGATCTTTG | TAGAAACCAT | 7980 |
| CGGCGCAGCT | ATTTACCCGC | AGGACATATC | CACGCCCTCC | TACATCGAAG | CTGAAAGCAC | 8040 |
| GAGATTCTTC | GCCCTCCGAG | AGCTGCATCA | GGTCGGAGAC | GCTGTCGAAC | TTTTCGATCA | 8100 |
| GAAACTTCTC | GACAGACGTC | GCGGTGAGTT | CAGGCTTTTT | CATATCTCAT | TGCCCCCGGG | 8160 |
| GGATCTGCGG | CACGCTGTTG | ACGCTGTTAA | GCGGGTCGCT | GCAGGGTCGC | TCGGTGTTCG | 8220 |
| AGGCCACACG | CGTCACCTTA | ATATGCGAAG | TGGACCTGGG | ACCGCGCCGC | CCCGACTGCA | 8280 |
| TCTGCGTGTT | CGAATTCGCC | AATGACAAGA | CGCTGGGCGG | GGTTTGTGTC | ATCATAGAAC | 8340 |
| TAAAGACATG | CAAATATATT | TCTTCCGGGG | ACACCGCCAG | CAAACGCGAG | CAACGGGCCA | 8400 |
| CGGGGATGAA | GCAGGCGGC | ACCTCGCTAA | CGGATTCACC | ACTCCAAGAA | TTGGAGCCAA | 8460 |
| TCAATTCTTG | CGGAGAACTG | TGAATGCGCA | AACCAACCCT | TGGCAGAACA | TATCCATCGC | 8520 |
| GTCCGCCATC | TCCAGCAGCC | GCACGCGGCG | CATCTCGGGC | AGGCCGACGC | GCTGGGCTAC | 8580 |
| GTCTTGCTGG | CGTTCGCGAC | GCGAGGCTGG | ATGGCCTTCC | CCATTATGAT | TCTTCTCGCT | 8640 |
| TCCGGCGGCA | TCGGGATGCC | CGCGTTGCAG | GCCATGCTGT | CCAGGCAGGT | AGATGACGAC | 8700 |
| CATCAGGGCA | GCAAAAGGCC | AGGAACCGTA | AAAAGGCCGC | GTTGCTGGCG | TTTTTCCATA | 8760 |
| GGCTCCGCCC | CCCTGACGAG | CATCACAAAA | ATCGACGCTC | AAGTCAGAGG | TGGCGAAACC | 8820 |
| CGACAGGACT | ATAAAGATAC | CAGGCGTTTC | CCCCTGGAAG | CTCCCTCGTG | CGCTCTCCTG | 8880 |
| TTCCGACCCT | GCCGCTTACC | GGATACCTGT | CCGCCTTTCT | CCCTTCGGGA | AGCGTGGCGC | 8940 |
| TTTCTCAATG | CTCACGCTGT | AGGTATCTCA | GTTCGGTGTA | GGTCGTTCGC | TCCAAGCTGG | 9000 |
| GCTGTGTGCA | CGAACCCCCC | GTTCAGCCCG | ACCGCTGCGC | CTTATCCGGT | AACTATCGTC | 9060 |
| TTGAGTCCAA | CCCGGTAAGA | CACGACTTAT | CGCCACTGGC | AGCAGCCACT | GGTAACAGGA | 9120 |

| | | | | | |
|---|---|---|---|---|---|
| TTAGCAGAGC | GAGGTATGTA | GGCGGTGCTA | CAGAGTTCTT | GAAGTGGTGG | CCTAACTACG | 9180 |
| GCTACACTAG | AAGGACAGTA | TTTGGTATCT | GCGCTCTGCT | GAAGCCAGTT | ACCTTCGGAA | 9240 |
| AAAGAGTTGG | TAGCTCTTGA | TCCGGCAAAC | AAACCACCGC | TGGTAGCGGT | GGTTTTTTTG | 9300 |
| TTTGCAAGCA | GCAGATTACG | CGCAGAAAAA | AAGGATCTCA | AGAAGATCCT | TTGATCTTTT | 9360 |
| CTACGGGGTC | TGACGCTCAG | TGGAACGAAA | ACTCACGTTA | AGGGATTTTG | GTCATGAGAT | 9420 |
| TATCAAAAAG | GATCTTCACC | TAGATCCTTT | TAAATTAAAA | ATGAAGTTTT | AAATCAATCT | 9480 |
| AAAGTATATA | TGAGTAAACT | TGGTCTGACA | GTTACCAATG | CTTAATCAGT | GAGGCACCTA | 9540 |
| TCTCAGCGAT | CTGTCTATTT | CGTTCATCCA | TAGTTGCCTG | ACTCCCGTC | GTGTAGATAA | 9600 |
| CTACGATACG | GGAGGGCTTA | CCATCTGGCC | CCAGTGCTGC | AATGATACCG | CGAGACCCAC | 9660 |
| GCTCACCGGC | TCCAGATTTA | TCAGCAATAA | ACCAGCCAGC | CGGAAGGGCC | GAGCGCAGAA | 9720 |
| GTGGTCCTGC | AACTTTATCC | GCCTCCATCC | AGTCTATTAA | TTGTTGCCGG | GAAGCTAGAG | 9780 |
| TAAGTAGTTC | GCCAGTTAAT | AGTTTGCGCA | ACGTTGTTGC | CATTGCTGCA | GGCATCGTGG | 9840 |
| TGTCACGCTC | GTCGTTTGGT | ATGGCTTCAT | TCAGCTCCGG | TTCCCAACGA | TCAAGGCGAG | 9900 |
| TTACATGATC | CCCCATGTTG | TGCAAAAAAG | CGGTTAGCTC | CTTCGGTCCT | CCGATCGTTG | 9960 |
| TCAGAAGTAA | GTTGGCCGCA | GTGTTATCAC | TCATGGTTAT | GGCAGCACTG | CATAATTCTC | 10020 |
| TTACTGTCAT | GCCATCCGTA | AGATGCTTTT | CTGTGACTGG | TGAGTACTCA | ACCAAGTCAT | 10080 |
| TCTGAGAATA | GTGTATGCGG | CGACCGAGTT | GCTCTTGCCC | GGCGTCAACA | CGGGATAATA | 10140 |
| CCGCGCCACA | TAGCAGAACT | TTAAAAGTGC | TCATCATTGG | AAAACGTTCT | TCGGGGCGAA | 10200 |
| AACTCTCAAG | GATCTTACCG | CTGTTGAGAT | CCAGTTCGAT | GTAACCCACT | CGTGCACCCA | 10260 |
| ACTGATCTTC | AGCATCTTTT | ACTTTCACCA | GCGTTTCTGG | GTGAGCAAAA | ACAGGAAGGC | 10320 |
| AAAATGCCGC | AAAAAAGGGA | ATAAGGGCGA | CACGGAAATG | TTGAATACTC | ATACTCTTCC | 10380 |
| TTTTTCAATA | TTATTGAAGC | ATTTATCAGG | GTTATTGTCT | CATGAGCGGA | TACATATTTG | 10440 |
| AATGTATTTA | GAAAAATAAA | CAAATAGGGG | TTCCGCGCAC | ATTTCCCCGA | AAAGTGCCAC | 10500 |
| CTGACGTCTA | AGAAACCATT | ATTATCATGA | CATTAACCTA | TAAAAATAGG | CGTATCACGA | 10560 |
| GGCCCTTTCG | TCTTCAAGAA | | | | | 10580 |

( 2 ) INFORMATION FOR SEQ ID NO:2:

( i ) SEQUENCE CHARACTERISTICS:
        ( A ) LENGTH: 11616 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( i v ) ANTI-SENSE: NO ( x ) PUBLICATION INFORMATION:
        ( H ) DOCUMENT NUMBER: WO PCT/DE91/00652
        ( I ) FILING DATE: 16-AUG-1991
        ( J ) PUBLICATION DATE: 04-MAR- 1993

( x i ) SEQUENCE DESCRIPTION: SEQ ID NO:2:

| | | | | | |
|---|---|---|---|---|---|
| GATCTCTAGA | ACTGGATACT | CGTGGGGGGT | AAAGAAGGTG | AATAAAAATT | ACAAACATTC | 60 |
| TCTGCCCAGC | CTTCAGACTA | TCAAACCTAG | ATAATCATTC | TATAAATAAC | CCAGGGCTTG | 120 |
| CATCACAATT | TAAAGGGAAG | TTAAGATGGG | GGATTACCTT | CTAAGAGGAA | ATGACAAGCC | 180 |
| ACAGACATCC | CCACATATAG | CCGGGTGTCC | ACTGTCTAAT | GTCAGTAATT | TAATTCCATA | 240 |

```
GTGAAAATAG CACCCCCAAC TCAATTTGGA ATCCAGAAAC TATATTGCAC ACCAACACCC      300
CCTCCTCTGC ACATGAGCAA GACAAGACAT CTATGTTTAT CTCTAAATGT GCCATGGAAC      360
CCGGTTGCCC ATGCAGTGGT GTCAGACAGG AAAATGGTTA ATTAACCACA TCTTAAATTG      420
CCACCTTAGG CAAATTGAAA ATAGGCAGGC TGAAGAATTG CACAATACCC TAAACAGGTA      480
AGAGGAATTA GTGACATTTT ATGAATTTTT TTACAAACTT TCACACTCAA GAATAGAAAC      540
CCAATACCAA CAGGTGTGCA GGTGTGCATG ACAAATCTTG GGGGTCTCAG AACCCAGGAC      600
CAGACTTTGA AGTCTCAGGT ATAGGTCCTG GCTGAGATTC TATTAATAAA ACAAGAGAGA      660
AAGAAGGCGG GCGCCCATTA GAATCTGCTC GGCTGCCAGT AAGTTGCCAG CAAACAGGAA      720
CACAAACAAA CCAAGGGTGT TGGCCCCTAC AGGCTCCCAA GGCGGGGGTT GGGCACAGGG      780
CCAAGCTCTG CCACCACAGG AGGCAAGTAG ACATGCAGGA ACACATGGCC CTGGCTAGGA      840
AAGGGAGGAA ATAGAGGCCA CAGCCAAAGT TAGGCTGCCG CCCCACCTGT GTACCCAGGG      900
TGAGAGACCT TGGGAGGTCG TCAGCTTAAC CAGCGCCGCC CTCACCCCAT TGCCAACTTC      960
CGGCTCACAC AAAACCACTC CCAAAAATTG AAGACTGGCC AAAATCCAGC TTCCGTCCCC     1020
GGGACGTGGT GCTTCCTAAA GGCGGGGCTC ATGGATTAGC AGGGGCTTAG TGTGTCATGG     1080
TGAGGCAGGC AAGGCGAGCA ACGGGGGCTT AGTGGCTCAA AGTGATGCAT CCCAAAGGCA     1140
GCCACCACGC TGGAGGGACA TTGTCCACGG GACAAGGCAC AGGCCAGGTC ATGACCCAGG     1200
AAGTGGCGAG CATCGGTCAG CTGACCAAAT GTGCAAAGGT GACAAGTCAG TAAGGCACGC     1260
GGGGGGCCAC GTCACCCCGG GGTGCTGGGG TGGGGATGG GCTCAGGCAA CCGTAAGGGA     1320
GGGGGGGGTA GGGGGGGGAG GGATTACACT ATAGGGTTCC CTTCCTCTAG GTTCTATATA     1380
CCTATAGGTA TATACCCAGC TGCAATACCC TATTCCACCA CTAGGTTAAT AACCTATAGG     1440
TTATTCTACC ATTAAAACGG AAGGAGGAAG GGTGGCGCAC CTTAAGGTAG GGTAGGGGGG     1500
TACCCCAGTA GGAACCTAGC TGAATCCTAC CTAGCTCCAC CCACCTGGTA TATAGGGGCG     1560
GAGCTTAGGA TACCTCCAGG ATAATGGAAC CCTATGGAGA CCTACCTCTA GGCTCCACCC     1620
ACTAGGTATA TCGGGGCGGA GCCCACTCCT CCCCCTCCTG GTTCAACCCT ATGGAGGGGA     1680
CCCTCCTGAG GCTCCGCCTA CCCCAAATCT CGCGGGCCTC TAGCCCCTCC TCCTCTCGTT     1740
ATCCCAATAG AATGACCTCC AGGTACCACC CACCTGGTTA CACACCTTAA TGTAACCCAA     1800
CGGGCTAAAA TCACACACCT GAATTAACCA ATGAGAAGCC CCCACACCT GAGCAAACCT     1860
TAAGGTATTG CACAGAAACC CCAAAAAGAG GATAAAAGAA GGCGAGCTGG CCCGGCTCGC     1920
CAGCGTCGTC CAGACGCTCG GGGGGTGCAC ACCTCCCAGC CGCAAGCTTG GCATTCCGGT     1980
ACTGTTGGTA AAATGGAAGA CGCCAAAAAC ATAAAGAAAG CCCGGCGCC ATTCTATCCT     2040
CTAGAGGATG GAACCGCTGG AGAGCAACTG CATAAGGCTA TGAAGAGATA CGCCCTGGTT     2100
CCTGGAACAA TTGCTTTTAC AGATGCACAT ATCGAGGTGA ACATCACGTA CGCGGAATAC     2160
TTCGAAATGT CCGTTCGGTT GGCAGAAGCT ATGAAACGAT ATGGGCTGAA TACAAATCAC     2220
AGAATCGTCG TATGCAGTGA AAACTCTCTT CAATTCTTTA TGCCGGTGTT GGGCGCGTTA     2280
TTTATCGGAG TTGCAGTTGC GCCCGCGAAC GACATTTATA ATGAACGTGA ATTGCTCAAC     2340
AGTATGAACA TTTCGCAGCC TACCGTAGTG TTTGTTTCCA AAAAGGGGTT GCAAAAAATT     2400
TTGAACGTGC AAAAAAAATT ACCAATAATC CAGAAAATTA TTATCATGGA TTCTAAAACG     2460
GATTACCAGG GATTTCAGTC GATGTACACG TTCGTCACAT CTCATCTACC TCCCGGTTTT     2520
AATGAATACG ATTTTGTACC AGAGTCCTTT GATCGTGACA AACAATTGC ACTGATAATG     2580
AATTCCTCTG GATCTACTGG GTTACCTAAG GGTGTGGCCC TTCCGCATAG AACTGCCTGC     2640
```

-continued

```
GTCAGATTCT CGCATGCCAG AGATCCTATT TTTGGCAATC AAATCATTCC GGATACTGCG    2700
ATTTTAAGTG TTGTTCCATT CCATCACGGT TTTGGAATGT TTACTACACT CGGATATTTG    2760
ATATGTGGAT TTCGAGTCGT CTTAATGTAT AGATTTGAAG AAGAGCTGTT TTTACGATCC    2820
CTTCAGGATT ACAAAATTCA AAGTGCGTTG CTAGTACCAA CCCTATTTTC ATTCTTCGCC    2880
AAAAGCACTC TGATTGACAA ATACGATTTA TCTAATTTAC ACGAAATTGC TTCTGGGGGC    2940
GCACCTCTTT CGAAAGAAGT CGGGGAAGCG GTTGCAAAAC GCTTCCATCT TCCAGGGATA    3000
CGACAAGGAT ATGGGCTCAC TGAGACTACA TCAGCTATTC TGATTACACC GAGGGGGAT    3060
GATAAACCGG GCGCGGTCGG TAAAGTTGTT CCATTTTTTG AAGCGAAGGT TGTGGATCTG    3120
GATACCGGGA AAACGCTGGG CGTTAATCAG AGAGGCGAAT TATGTGTCAG AGGACCTATG    3180
ATTATGTCCG GTTATGTAAA CAATCCGGAA GCGACCAACG CCTTGATTGA CAAGGATGGA    3240
TGGCTACATT CTGGAGACAT AGCTTACTGG GACGAAGACG AACACTTCTT CATAGTTGAC    3300
CGCTTGAAGT CTTTAATTAA ATACAAAGGA TATCAGGTGG CCCCCGCTGA ATTGGAATCG    3360
ATATTGTTAC AACACCCCAA CATCTTCGAC GCGGGCGTGG CAGGTCTTCC CGACGATGAC    3420
GCCGGTGAAC TTCCCGCCGC CGTTGTTGTT TTGGAGCACG GAAAGACGAT GACGGAAAAA    3480
GAGATCGTGG ATTACGTCGC CAGTCAAGTA ACAACCGCGA AAAGTTGCG CGGAGGAGTT    3540
GTGTTTGTGG ACGAAGTACC GAAAGGTCTT ACCGGAAAAC TCGACGCAAG AAAAATCAGA    3600
GAGATCCTCA TAAAGGCCAA GAAGGGCGGA AAGTCCAAAT TGTAAAATGT AACTGTATTC    3660
AGCGATGACG AAATTCTTAG CTATTGTAAT GACTCTAGAG GATCTTTGTG AAGGAACCTT    3720
ACTTCTGTGG TGTGACATAA TTGGACAAAC TACCTACAGA GATTTAAAGC TCTAAGGTAA    3780
ATATAAAATT TTTAAGTGTA TAATGTGTTA AACTACTGAT TCTAATTGTT TGTGTATTTT    3840
AGATTCCAAC CTATGGAACT GATGAATGGG AGCAGTGGTG AATGCCTTT AATGAGGAAA    3900
ACCTGTTTTG CTCAGAAGAA ATGCCATCTA GTGATGATGA GGCTACTGCT GACTCTCAAC    3960
ATTCTACTCC TCCAAAAAAG AAGAGAAAGG TAGAAGACCC CAAGGACTTT CCTTCAGAAT    4020
TGCTAAGTTT TTTGAGTCAT GCTGTGTTTA GTAATAGAAC TCTTGCTTGC TTTGCTATTT    4080
ACACCACAAA GGAAAAAGCT GCACTGCTAT ACAAGAAAAT TATGGAAAAA TATTCTGTAA    4140
CCTTTATAAG TAGGCATAAC AGTTATAATC ATAACATACT GTTTTTCTT ACTCCACACA    4200
GGCATAGAGT GTCTGCTATT AATAACTATG CTCAAAAATT GTGTACCTTT AGCTTTTTAA    4260
TTTGTAAAGG GGTTAATAAG GAATATTTGA TGTATAGTGC CTTGACTAGA GATCATAATC    4320
AGCCATACCA CATTTGTAGA GGTTTTACTT GCTTTAAAAA ACCTCCCACA CCTCCCCCTG    4380
AACCTGAAAC ATAAAATGAA TGCAATTGTT GTTGTTAACT TGTTATTGC AGCTTATAAT    4440
GGTTACAAAT AAAGCAATAG CATCACAAAT TCACAAATA AAGCATTTT TCACTGCAT    4500
TCTAGTTGTG GTTTGTCCAA ACTCATCAAT GTATCTTATC ATGTCTGGAT CCTCTACGCC    4560
GGACGCATCG TGGCCGGCAT CACCGGCGCC ACAGGTGCGG TTGCTGGCGC CTATATCGCC    4620
GACATCACCG ATGGGGAAGA TCGGGCTCGC CACTTCGGGC TCATGAGCGC TTGTTTCGGC    4680
GTGGGTATGG TGGCAGGCCC CGTGGCCGGG GGACTGTTGG GCGCCATCTC CTTGCATGCA    4740
CCATTCCTTG CGGCGGCGGT GCTCAACGGC CTCAACCTAC TACTGGGCTG CTTCCTAATG    4800
CAGGAGTCGC ATAAGGGAGA GCGTCGACTA CGCGATCATG GCGACCACAC CGTCTCGAC    4860
CGATGCCCTT GAGAGCCTTC AACCCAGTCA GCTCCTTCCG GTGGGCGCGG GGCATGACTA    4920
TCGTCGCCGC ACTTATGACT GTCTTCTTTA TCATGCAACT CGTAGGACAG GTGCCCTGGC    4980
CGGGGTCCCG CGGAAACTCG GCCGTGGTGA CAGGAAAAGG ACAAGCAGCG AAAATTCACG    5040
```

```
CCCCCTTGGG AGGTGGCGGC ATATGCAAAG GATAGCACTC CCACTCTACT ACTGGGTATC     5100
ATATGCTGAC TGTATATGCA TGAGGATAGC ATATGCTACC CGGATACAGA TTAGGATAGC     5160
ATATACTACC CAGATATAGA TTAGGATAGC ATATGCTACC CAGATATAGA TTAGGATAGC     5220
CTATGCTACC CAGATATAAA TTAGGATAGC ATATACTACC CAGATATAGA TTAGGATAGC     5280
ATATGCTACC CAGATATAGA TTAGGATAGC CTATGCTACC CAGATATAGA TTAGGATAGC     5340
ATATGCTACC CAGATATAGA TTAGGATAGC ATATGCTATC CAGATATTTG GGTAGTATAT     5400
GCTACCCAGA TATAAATTAG GATAGCATAT ACTACCCTAA TCTCTATTAG GATAGCATAT     5460
GCTACCCGGA TACAGATTAG GATAGCATAT ACTACCCAGA TATAGATTAG GATAGCATAT     5520
GCTACCCAGA TATAGATTAG GATAGCCTAT GCTACCCAGA TATAAATTAG GATAGCATAT     5580
ACTACCCAGA TATAGATTAG GATAGCATAT GCTACCCAGA TATAGATTAG GATAGCCTAT     5640
GCTACCCAGA TATAGATTAG GATAGCATAT GCTATCCAGA TATTTGGGTA GTATATGCTA     5700
CCCATGGCAA CATTAGCCCA CCGTGCTCTC AGCGACCTCG TGAATATGAG GACCAACAAC     5760
CCTGTGCTTG GCGCTCAGGC GCAAGTGTGT GTAATTTGTC CTCCAGATCG CAGCAATCGC     5820
GCCCCTATCT TGGCCCGCCC ACCTACTTAT GCAGGTATTC CCGGGGTGC CATTAGTGGT     5880
TTTGTGGGCA AGTGGTTTGA CCGCAGTGGT TAGCGGGGTT ACAATCAGCC AAGTTATTAC     5940
ACCCTTATTT TACAGTCCAA AACCGCAGGG CGGCGTGTGG GGGCTGACGC GTGCCCCAC     6000
TCCACAATTT CAAAAAAAG AGTGGCCACT TGTCTTTGTT TATGGGCCCC ATTGGCGTGG     6060
AGCCCGTTT AATTTTCGGG GGTGTTAGAG ACAACCAGTG GAGTCCGCTG CTGTCGGCGT     6120
CCACTCTCTT TCCCCTTGTT ACAAATAGAG TGTAACAACA TGGTTCACCT GTCTTGGTCC     6180
CTGCCTGGGA CACATCTTAA TAACCCCAGT ATCATATTGC ACTAGGATTA TGTGTTGCCC     6240
ATAGCCATAA ATTCGTGTGA GATGGACATC CAGTCTTTAC GGCTTGTCCC CACCCCATGG     6300
ATTTCTATTG TTAAAGATAT TCAGAATGTT TCATTCCTAC ACTAGTATTT ATTGCCCAAG     6360
GGGTTTGTGA GGGTTATATT GGTGTCATAG CACAATGCCA CCACTGAACC CCCCGTCCAA     6420
ATTTTATTCT GGGGGCGTCA CCTGAAACCT TGTTTCGAG CACCTCACAT ACACCTTACT     6480
GTTCACAACT CAGCAGTTAT TCTATTAGCT AAACGAAGGA GAATGAAGAA GCAGGCGAAG     6540
ATTCAGGAGA GTTCACTGCC CGCTCCTTGA TCTTCAGCCA CTGCCCTTGT GACTAAAATG     6600
GTTCACTACC CTCGTGGAAT CCTGACCCCA TGTAAATAAA ACCGTGACAG CTCATGGGGT     6660
GGGAGATATC GCTGTTCCTT AGGACCCTTT TACTAACCCT AATTCGATAG CATATGCTTC     6720
CCGTTGGGTA ACATATGCTA TTGAATTAGG GTTAGTCTGG ATAGTATATA CTACTACCCG     6780
GGAAGCATAT GCTACCCGTT TAGGGTTAAC AAGGGGGCCT TATAAACACT ATTGCTAATG     6840
CCCTCTTGAG GGTCCGCTTA TCGGTAGCTA CACAGGCCCC TCTGATTGAC GTTGGTGTAG     6900
CCTCCCGTAG TCTTCCTGGG CCCCTGGGAG GTACATGTCC CCAGCATTG GTGTAAGAGC     6960
TTCAGCCAAG AGTTACACAT AAAGGCAATG TTGTGTTGCA GTCCACAGAC TGCAAAGTCT     7020
GCTCCAGGAT GAAAGCCACT CAGTGTTGGC AAATGTGCAC ATCCATTTAT AAGGATGTCA     7080
ACTACAGTCA GAGAACCCCT TTGTGTTTGG TCCCCCCCG TGTCACATGT GGAACAGGGC     7140
CCAGTTGGCA AGTTGTACCA ACCAACTGAA GGGATTACAT GCACTGCCCC GTGACCAATA     7200
CAAAACAAAA GCGCTCCTCG TACCAGCGAA GAAGGGGCAG AGATGCCGTA GTCAGGTTTA     7260
GTTCGTCCGG CGGCGCCAGA AATCCGCGCG GTGGTTTTTG GGGGTCGGGG GTGTTTGGCA     7320
GCCACAGACG CCCGGTGTTC GTGTCGCGCC AGTACATGCG GTCCATGCCC AGGCCATCCA     7380
AAAACCATGG GTCTGTCTGC TCAGTCCAGT CGTGGACCTG ACCCCACGCA ACGCCCAAAA     7440
```

```
GAATAACCCC CACGAACCAT AAACCATTCC CCATGGGGA CCCCGTCCCT AACCCACGGG   7500
GCCCGTGGCT ATGGCGGGCT TGCCGCCCCG ACGTTGGCTG CGAGCCCTGG GCCTTCACCC   7560
GAACTTGGGG GTTGGGGTGG GGAAAAGGAA GAAACGCGGG CGTATTGGCC CCAATGGGGT   7620
CTCGGTGGGG TATCGACAGA GTGCCAGCCC TGGGACCGAA CCCCGCGTTT ATGAACAAAC   7680
GACCCAACAC CCGTGCGTTT TATTCTGTCT TTTTATTGCC GTCATAGCGC GGGTTCCTTC   7740
CGGTATTGTC TCCTTCCGTG TTTCAGTTAG CCTCCCCAT CTCCGATCC CCTCGGACGA   7800
GTGCTGGGGC GTCGGTTTCC ACTATCGGCG AGTACTTCTA CACAGCCATC GGTCCAGACG   7860
GCCGCGCTTC TGCGGGCGAT TTGTGTACGC CCGACAGTCC CGGCTCCGGA TCGGACGATT   7920
GCGTCGCATC GACCCTGCGC CCAAGCTGCA TCATCGAAAT TGCCGTCAAC CAAGCTCTGA   7980
TAGAGTTGGT CAAGACCAAT GCGGAGCATA TACGCCCGGA GCCGCGGCGA TCCTGCAAGC   8040
TCCGGATGCC TCCGCTCGAA GTAGCGCGTC TGCTGCTCCA TACAAGCCAA CCACGGCCTC   8100
CAGAAGAAGA TGTTGGCGAC CTCGTATTGG GAATCCCCGA ACATCGCCTC GCTCCAGTCA   8160
ATGACCGCTG TTATGCGGCC ATTGTCCGTC AGGACATTGT TGGAGCCGAA ATCCGCGTGC   8220
ACGAGGTGCC GGACTTCGGG GCAGTCCTCG GCCCAAAGCA TCAGCTCATC GAGAGCCTGC   8280
GCGACGGACG CACTGACGGT GTCGTCCATC ACAGTTTGCC AGTGATACAC ATGGGGATCA   8340
GCAATCGCGC ATATGAAATC ACGCCATGTA GTGTATTGAC CGATTCCTTG CGGTCCGAAT   8400
GGGCCGAACC CGCTCGTCTG GCTAAGATCG GCCGCAGCGA TCGCATCCAT GGCCTCCGCG   8460
ACCGGCTGCA GAACAGCGGG CAGTTCGGTT TCAGGCAGGT CTTGCAACGT GACACCCTGT   8520
GCACGGCGGG AGATGCAATA GGTCAGGCTC TCGCTGAATT CCCCAATGTC AAGCACTTCC   8580
GGAATCGGGA GCGCGGCCGA TGCAAAGTGC CGATAAACAT AACGATCTTT GTAGAAACCA   8640
TCGGCGCAGC TATTTACCCG CAGGACATAT CCACGCCCTC CTACATCGAA GCTGAAAGCA   8700
CGAGATTCTT CGCCCTCCGA GAGCTGCATC AGGTCGGAGA CGCTGTCGAA CTTTTCGATC   8760
AGAAACTTCT CGACAGACGT CGCGGTGAGT TCAGGCTTTT TCATATCTCA TTGCCCCGG   8820
GGGATCTGCG GCACGCTGTT GACGCTGTTA AGCGGGTCGC TGCAGGGTCG CTCGGTGTTC   8880
GAGGCCACAC GCGTCACCTT AATATGCGAA GTGGACCTGG GACCGCGCCG CCCCGACTGC   8940
ATCTGCGTGT TCGAATTCGC CAATGACAAG ACGCTGGGCG GGGTTTGTGT CATCATAGAA   9000
CTAAAGACAT GCAAATATAT TTCTTCCGGG GACACCGCCA GCAAACGCGA GCAACGGGCC   9060
ACGGGGATGA AGCAGGGCGG CACCTCGCTA ACGGATTCAC CACTCCAAGA ATTGGAGCCA   9120
ATCAATTCTT GCGGAGAACT GTGAATGCGC AAACCAACCC TTGGCAGAAC ATATCCATCG   9180
CGTCCGCCAT CTCCAGCAGC CGCACGCGGC GCATCTCGGG CAGGCCGACG CGCTGGGCTA   9240
CGTCTTGCTG GCGTTCGCGA CGCGAGGCTG GATGGCCTTC CCCATTATGA TTCTTCTCGC   9300
TTCCGGCGGC ATCGGGATGC CCGCGTTGCA GGCCATGCTG TCCAGGCAGG TAGATGACGA   9360
CCATCAGGGC AGCAAAAGGC CAGGAACCGT AAAAAGGCCG CGTTGCTGGC GTTTTTCCAT   9420
AGGCTCCGCC CCCCTGACGA GCATCACAAA AATCGACGCT CAAGTCAGAG GTGGCGAAAC   9480
CCGACAGGAC TATAAAGATA CCAGGCGTTT CCCCCTGGAA GCTCCCTCGT GCGCTCTCCT   9540
GTTCCGACCC TGCCGCTTAC CGGATACCTG TCCGCCTTTC TCCCTTCGGG AAGCGTGGCG   9600
CTTTCTCAAT GCTCACGCTG TAGGTATCTC AGTTCGGTGT AGGTCGTTCG CTCCAAGCTG   9660
GGCTGTGTGC ACGAACCCCC CGTTCAGCCC GACCGCTGCG CCTTATCCGG TAACTATCGT   9720
CTTGAGTCCA ACCCGGTAAG ACACGACTTA TCGCCACTGG CAGCAGCCAC TGGTAACAGG   9780
ATTAGCAGAG CGAGGTATGT AGGCGGTGCT ACAGAGTTCT TGAAGTGGTG GCCTAACTAC   9840
```

| | | | | | | |
|---|---|---|---|---|---|---|
| GGCTACACTA | GAAGGACAGT | ATTTGGTATC | TGCGCTCTGC | TGAAGCCAGT | TACCTTCGGA | 9900 |
| AAAAGAGTTG | GTAGCTCTTG | ATCCGGCAAA | CAAACCACCG | CTGGTAGCGG | TGGTTTTTTT | 9960 |
| GTTTGCAAGC | AGCAGATTAC | GCGCAGAAAA | AAAGGATCTC | AAGAAGATCC | TTTGATCTTT | 10020 |
| TCTACGGGGT | CTGACGCTCA | GTGGAACGAA | AACTCACGTT | AAGGGATTTT | GGTCATGAGA | 10080 |
| TTATCAAAAA | GGATCTTCAC | CTAGATCCTT | TTAAATTAAA | AATGAAGTTT | TAAATCAATC | 10140 |
| TAAAGTATAT | ATGAGTAAAC | TTGGTCTGAC | AGTTACCAAT | GCTTAATCAG | TGAGGCACCT | 10200 |
| ATCTCAGCGA | TCTGTCTATT | TCGTTCATCC | ATAGTTGCCT | GACTCCCCGT | CGTGTAGATA | 10260 |
| ACTACGATAC | GGGAGGGCTT | ACCATCTGGC | CCCAGTGCTG | CAATGATACC | GCGAGACCCA | 10320 |
| CGCTCACCGG | CTCCAGATTT | ATCAGCAATA | AACCAGCCAG | CCGGAAGGGC | CGAGCGCAGA | 10380 |
| AGTGGTCCTG | CAACTTTATC | CGCCTCCATC | CAGTCTATTA | ATTGTTGCCG | GGAAGCTAGA | 10440 |
| GTAAGTAGTT | CGCCAGTTAA | TAGTTTGCGC | AACGTTGTTG | CCATTGCTGC | AGGCATCGTG | 10500 |
| GTGTCACGCT | CGTCGTTTGG | TATGGCTTCA | TTCAGCTCCG | GTTCCCAACG | ATCAAGGCGA | 10560 |
| GTTACATGAT | CCCCCATGTT | GTGCAAAAAA | GCGGTTAGCT | CCTTCGGTCC | TCCGATCGTT | 10620 |
| GTCAGAAGTA | AGTTGGCCGC | AGTGTTATCA | CTCATGGTTA | TGGCAGCACT | GCATAATTCT | 10680 |
| CTTACTGTCA | TGCCATCCGT | AAGATGCTTT | TCTGTGACTG | GTGAGTACTC | AACCAAGTCA | 10740 |
| TTCTGAGAAT | AGTGTATGCG | GCGACCGAGT | TGCTCTTGCC | CGGCGTCAAC | ACGGGATAAT | 10800 |
| ACCGCGCCAC | ATAGCAGAAC | TTTAAAAGTG | CTCATCATTG | GAAAACGTTC | TTCGGGGCGA | 10860 |
| AAACTCTCAA | GGATCTTACC | GCTGTTGAGA | TCCAGTTCGA | TGTAACCCAC | TCGTGCACCC | 10920 |
| AACTGATCTT | CAGCATCTTT | TACTTTCACC | AGCGTTTCTG | GGTGAGCAAA | AACAGGAAGG | 10980 |
| CAAAATGCCG | CAAAAAAGGG | AATAAGGGCG | ACACGGAAAT | GTTGAATACT | CATACTCTTC | 11040 |
| CTTTTTCAAT | ATTATTGAAG | CATTTATCAG | GGTTATTGTC | TCATGAGCGG | ATACATATTT | 11100 |
| GAATGTATTT | AGAAAAATAA | ACAAATAGGG | GTTCCGCGCA | CATTTCCCCG | AAAAGTGCCA | 11160 |
| CCTGACGTCT | AAGAAACCAT | TATTATCATG | ACATTAACCT | ATAAAAATAG | GCGTATCACG | 11220 |
| AGGCCCTTTC | GTCTTCAAGA | ATTCTCATGT | TTGACAGCTT | ATCATCGATA | AGCTTTAATG | 11280 |
| CGGTAGTTTA | TCACAGTTAA | ATTGCTAACG | CAGTCAGGCA | CCGTGTATGA | AATCTAACAA | 11340 |
| TGCGCTCATC | GTCATCCTCG | GCACCGTCAC | CCTGGATGCT | GTAGGCATAG | GCTTGGTTAT | 11400 |
| GCCGGTACTG | CCGGGCCTCT | TGCGGGATAT | CGTCCATTCC | GACAGCATCG | CCAGTCACTA | 11460 |
| TGGCGTGCTG | CTAGCGCTAT | ATGCGTTGAT | GCAATTTCTA | TGCGCACCCG | TTCTCGGAGC | 11520 |
| ACTGTCCGAC | CGCTTTGGCC | GCCGCCCAGT | CCTGCTCGCT | TCGCTACTTG | GAGCCACTAT | 11580 |
| CGACTACGCG | ATCATGGCGA | CCACACCCGT | CCTGTG | | | 11616 |